(12) United States Patent
Ramesh et al.

(10) Patent No.: US 10,433,726 B2
(45) Date of Patent: Oct. 8, 2019

(54) SYSTEMS, METHODS, AND DEVICES FOR REMOTE HEALTH MONITORING AND MANAGEMENT USING INTERNET OF THINGS SENSORS

(71) Applicant: Amrita Vishwa Vidyapeetham, Tamil Nadu (IN)

(72) Inventors: Maneesha Vinodini Ramesh, Kerala (IN); Rahul Krishnan Pathinarupothi, Kerala (IN); Ekanath Srihari Rangan, Tamil Nadu (IN); Durga P, Kerala (IN); P. Venkat Rangan, Tamil Nadu (IN)

(73) Assignee: Amrita Vishwa Vidyapeetham (IN)

( * ) Notice: Subject to any disclaimer, the term of this patent is extended or adjusted under 35 U.S.C. 154(b) by 0 days.

(21) Appl. No.: 16/117,689

(22) Filed: Aug. 30, 2018

(65) Prior Publication Data

US 2019/0046037 A1 Feb. 14, 2019

Related U.S. Application Data

(63) Continuation-in-part of application No. 16/103,159, filed on Aug. 14, 2018.

(51) Int. Cl.
| | | |
|---|---|---|
| A61B 5/00 | (2006.01) | |
| A61B 5/0205 | (2006.01) | |
| H04L 29/08 | (2006.01) | |
| G16H 40/67 | (2018.01) | |
| G16H 40/63 | (2018.01) | |
| G16H 50/20 | (2018.01) | |

(Continued)

(52) U.S. Cl.
CPC .......... *A61B 5/0022* (2013.01); *A61B 5/0024* (2013.01); *A61B 5/0205* (2013.01); *G16H 40/63* (2018.01); *G16H 40/67* (2018.01); *G16H 50/20* (2018.01); *H04L 67/12* (2013.01); *A61B 5/0006* (2013.01); *A61B 5/046* (2013.01); *A61B 5/0464* (2013.01); *A61B 5/0468* (2013.01); *A61B 5/0472* (2013.01); *A61B 5/14532* (2013.01); *A61B 5/7275* (2013.01); *H04L 67/18* (2013.01); *H04L 67/30* (2013.01); *H04L 67/322* (2013.01)

(58) Field of Classification Search
CPC ... A61B 5/0022; A61B 5/0006; A61B 5/0205; A61B 5/046; A61B 5/0464; A61B 5/0468; A61B 5/0472; A61B 5/14532; G16H 40/67; H04L 67/12; H04L 67/18; H04L 67/30; H04L 67/322
USPC ....................................... 340/870.2
See application file for complete search history.

(56) References Cited

U.S. PATENT DOCUMENTS

| | | | |
|---|---|---|---|
| 10,022,614 B1 * | 7/2018 | Tran ...................... | A63B 71/145 |
| 2014/0121476 A1 * | 5/2014 | Tran ...................... | A61B 5/0024 |
| | | | 600/301 |

(Continued)

*Primary Examiner* — Hirdepal Singh
(74) *Attorney, Agent, or Firm* — Donald R. Boys; Central Coast Patent Agency, LLC

(57) ABSTRACT

A health-monitoring system has IoT-vitals sensing nodes joined to a patient's body, sensing vital characteristics, employing wireless transmission circuitry transmitting sensed data by a short-range network, and a local gateway having wireless circuitry receiving transmitted data from the IoT-vitals sensors, software (SW) executing on a processor from a non-transitory medium, the SW processing the transmitted data received, and transmission circuitry transmitting processed data over a long-range network.

22 Claims, 23 Drawing Sheets

(51) Int. Cl.
    *A61B 5/046*     (2006.01)
    *A61B 5/0468*    (2006.01)
    *A61B 5/0464*    (2006.01)
    *A61B 5/145*     (2006.01)
    *A61B 5/0472*    (2006.01)

(56) References Cited

U.S. PATENT DOCUMENTS

| | | | |
|---|---|---|---|
| 2017/0006141 A1* | 1/2017 | Bhadra | H04L 67/12 |
| 2017/0177811 A1* | 6/2017 | McFarland | G06F 19/3456 |
| 2017/0244814 A1* | 8/2017 | Yin | H04L 69/08 |
| 2018/0102035 A1* | 4/2018 | Trishaun | G08B 21/0211 |
| 2018/0184980 A1* | 7/2018 | Qin | A61B 5/6843 |
| 2018/0256029 A1* | 9/2018 | Deshpande et al. | G06Q 10/10 |
| 2018/0353137 A1* | 12/2018 | Balajadia | A61B 5/7278 |
| 2019/0046056 A1* | 2/2019 | Khachaturian | G16H 40/63 |

* cited by examiner

| Power Management Factors | | Battery Level | | |
|---|---|---|---|---|
| Location | Priority | Low | Medium | High |
| In-ward Telemetry | Routine | Delayed | Immediate | Immediate |
| | Critical | Immediate | Immediate | Immediate |
| Outdoor | Routine | Delayed | Delayed | Local PAS + Delayed |
| | Critical | Immediate | Immediate | Local PAS + Immediate |
| Indoor | Routine | Local PAS + Delayed | Local PAS + Immediate | Local PAS + Immediate |
| | Critical | Immediate | Immediate | Local PAS + Immediate |

SYSTEMS, METHODS, AND DEVICES FOR REMOTE HEALTH MONITORING AND MANAGEMENT USING INTERNET OF THINGS SENSORS

CROSS-REFERENCE TO RELATED APPLICATIONS

The present application claims priority to co-pending U.S. patent application Ser. No. 16/103,159, filed Aug. 14, 2018, which claims priority to Indian Patent Application No. 201741028828, filed on Aug. 14, 2017. All disclosure of the parent cases is incorporated herein at least by reference.

FIELD OF THE INVENTION

The invention generally relates to body sensor tracking and monitoring platforms, and in particular, to health monitoring systems, methods, and devices to remotely monitor and track patient health status.

DESCRIPTION OF RELATED ART

Present healthcare technologies allow for body sensors or implants attached to a patient to be used in medical monitoring and detection of emergency conditions in at-risk patients. However, the patient usually has to present himself at a local healthcare facility for accurate measurements, gain access to Hospital Information Systems (HIS) and advanced analytics, and subsequently wait for the assessment of the data by the Health Service Provider (HSP). Remote monitoring of the patient is greatly desired in such patients as it allows for continuous monitoring of the patient without disrupting their normal lives, provides access from remote areas that lack good healthcare facilities, allows intervention by specialized practitioners, and sharing of resource or information in the existing healthcare facilities.

Various publications have attempted to remote healthcare services. For example, U.S. Pat. No. 7,978,062B2 discloses medical data transport over wireless life critical network. US20150066538A1 discloses a communication device resource allocation based on medical data criticality and resource status. U.S. Pat. No. 9,186,077B2 discloses method and devices with customizable power management providing wireless communication of heart rate data of users. Although systems for managing medical conditions have been described, they are largely limited to urban areas with good infrastructure and connectivity. There remains a need to provide monitoring methods and systems from remote areas that are sparsely connected, and leverage Internet-of-Things (IoT) technology in wearable sensors.

Furthermore, there remains a need for access to relevant medical information, processing, analytics and communication for timely intervention of an adverse event occurring in patients located in remote areas while excluding minor aberrational data that may not be indicative of any serious condition.

SUMMARY OF THE INVENTION

In an embodiment of the invention a health-monitoring system is provided, comprising IoT-vitals sensing nodes joined to a patient's body, sensing vital characteristics, employing wireless transmission circuitry transmitting sensed data by a short-range network, and a local gateway having wireless circuitry receiving transmitted data from the IoT-vitals sensors, software (SW) executing on a processor from a non-transitory medium, the SW processing the transmitted data received, and transmission circuitry transmitting processed data over a long-range network.

In one embodiment of the system he sensing nodes comprise at least one electrocardiology (ECG) sensor and at least one photoplethysmography (PPG) sensor. Also in one embodiment one sensor is configured as a master sensor and one or more other sensors are configured as slave sensors, the master sensor receiving data from the slave sensors and transmitting the received data to the gateway. In one embodiment the short-range network is one of ZigBee™, Bluetooth™ or WiFi. And in one embodiment the long-range network is one of a cellular network, a radio-frequency network or the Internet network.

In one embodiment the SW executing on the gateway comprises separate programs, a first program accomplishing rapid summarization of data for transmission to one remote destination as personalized health motifs (PHM), and a second program computing criticality alerts from the PHM data. Also in one embodiment the summarized data is transmitted from the gateway to a cloud-storage and processing center, and the criticality alerts are transmitted by a second data network to doctor's platforms. In one embodiment the gateway is accomplished by a smartphone executing software providing functions of the gateway. In one embodiment the doctor's platforms execute Android-based SW enabling the doctors to receive and visualize patient data, and to suggest interventions remotely to the patients or their caretakers. And in one embodiment the Android-based SW also enable the doctors to set and tune sensing frequency, transmission timing, summarization intervals, and other variables in the system.

In one embodiment of the cloud broadly hosts a Hospital Information System (HIS) software suite and data storage which is a publicly available CCHIT certified J2EE based health informatics suite. In one embodiment HIS serves as an archival database storage for all patient records with access control, security, privacy, and reliability. And oin one embodiment HIS additionally supports running special purpose data analytics algorithms on anonymized patient data.

In another aspect of the invention a method for monitoring a patient's vital medical characteristics is provided, comprising joining IoT-vitals sensing nodes to the patient's body, sensing vital characteristics, transmitting sensed data to a gateway by a short-range network, receiving the transmitted data at a gateway, processing the data received by software (SW) executing on a processor at the gateway, and transmitting the processed data over a long-range network.

In one embodiment the method comprises sensing electrocardiology (ECG) data by one sensing node, and sensing photoplethysmography (PPG) data by another sensor. Also in one embodiment the method comprises one sensor operating as a master sensor, and one or more other sensors operating as slave sensors, the master sensor receiving data from the slave sensors and transmitting the received data to the gateway. In one embodiment sensors transmit by one of ZigBee™, Bluetooth™ or WiFi protocol. In one embodiment the gateway transmits by one of cellular, radio frequency or Internet protocol. In one embodiment a first program executing on the gateway accomplishes rapid summarization of data for transmission to one remote destination as personalized health motifs (PHM), and a second program computes criticality alerts from the PHM data. And in one embodiment the summarized data is transmitted from the gateway to a cloud-storage and processing center, and the criticality alerts are transmitted by a second data network to doctor's platforms.

In one embodiment of the method the gateway is accomplished by a smartphone executing software providing functions of the gateway. In one embodiment the doctor's platforms execute Android-based SW enabling the doctors to receive and visualize patient data, and to suggest interventions remotely to the patients or their caretakers. And in one embodiment the Android-based SW also enables the doctors to set and tune sensing frequency, transmission timing, summarization intervals, and other variables in the system.

In one embodiment of the method the cloud broadly hosts a Hospital Information System (HIS) software suite and data storage which is a publicly available CCHIT certified J2EE based health informatics suite. In one embodiment HIS serves as an archival database storage for all patient records with access control, security, privacy, and reliability. And in one embodiment HIS additionally supports running special purpose data analytics algorithms on anonymized patient data.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 5D illustrates a power management mechanism based on patient location and data priority.

DETAILED DESCRIPTION OF THE INVENTION

Figure 1A:
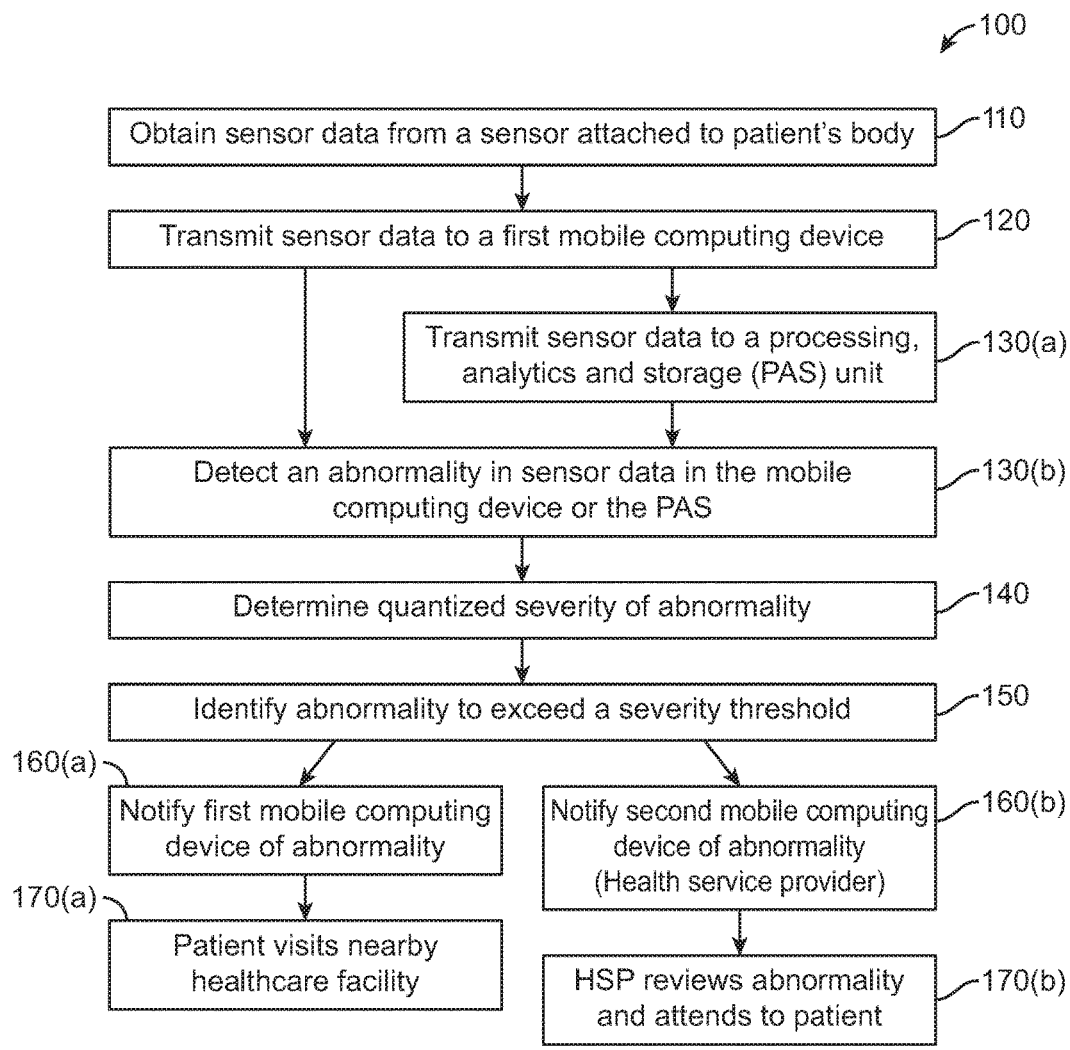
FIG. 1A shows a method for remote health monitoring of patients.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The present disclosure describes systems, methods, devices, and kits for remote monitoring and tracking of patient health status using one or more sensors, location- and power-aware communication systems and analytics. In one embodiment, a system for use in remote monitoring of a patient is provided. In another embodiment, the invention relates to a method of remote monitoring and tracking of patient health status even in sparsely connected and remote regions. In various embodiments the invention discloses system of rapid summarization for effective prognosis in wireless remote health monitoring (RASPRO). In yet other embodiments, a computer program product for remote monitoring of a patient is provided.

A method 100 for remote monitoring of a patient is provided herein, as illustrated in FIG. 1A. The method includes obtaining sensor data from one or more sensors attached to a patient's body in block 110. In block 120, the data is aggregated by a data aggregation and transmission unit and transmitted to a first mobile computing device through a wired or a short-range wireless communication network. The next step may involve transmitting the sensor data to a processing, analytics and storage (PAS) unit through a wireless communication network in block 130(a). One or more abnormalities may be detected in the sensor data by periodic assessment of the sensor data in block 130(b). The processing may be either carried out in the first mobile computing device, or the PAS unit. In some embodiments, the method 100 further includes determining a quantized severity for the one or more abnormalities detected in block 140. The method includes identifying that the severity of the one or more abnormalities exceeds a severity threshold for the patient, in block 150. The severity threshold for the patient in some embodiments may be a set of predetermined values derived from sensor data, inter-sensor correlation, patient's historical data, doctor's inputs, inter-patient machine learning models, or a combination thereof. The next step 160(a) or 160(b) involves sending a notification of the one or more abnormalities to the first mobile computing device and the second mobile computing device associated with the Health Service Provider (HSP). In some embodiments sending a notification of the abnormality to the second mobile computing device includes presenting patient health status to health service provider based on the criticality of data. In some embodiments, the method may further include analyzing the sensor data by visualization, monitoring, analysis or intervention tools by the health service provider. The notification may also include an estimate of time available to the HSP for effective intervention. In one embodiment, the method may additionally include directing a doctor, hospital, caregiver, or emergency responder to attend to the patient, in block step 170(b). In one embodiment, the medium of notification of the second mobile computing device in block 160(b) is determined based on data criticality, patient profile, available communication media, power availability of the mobile computing devices and sensors, location of the at least one processing, analytics and storage (PAS) unit, or a combination thereof. In an alternate embodiment, in block 170(a), the patient may visit a nearby healthcare facility to obtain medical attention.

In some embodiments, block 110 of the method 100 includes obtaining a sensor signal such as blood pressure level, a blood glucose level, an oxygen saturation (SpO2) level, an electrocardiogram (ECG) data, motion detection system data, accelerometer data, GPS data, or a combination thereof. In some embodiments, detecting the one or more abnormality in sensor data in block 130(b) involves detecting an abnormality that is indicative of a cardiovascular disease in the patient. In various embodiments, transmitting the sensor data to the first mobile computing device in step 120 includes transmitting over a GSM, 2G, 3G, 4G, LTE, Wi-Fi network or an Ad-hoc network created with neighboring wireless terminals. In one embodiment block 120 may additionally include transmitting the sensor data to one or more mobile computing devices or to HSP device over a wireless network. In various embodiments, transmitting the sensor data to the processing, analytics and storage (PAS) unit in block 130(a) includes transmitting to a local PAS unit, a remote PAS unit, a hospital PAS unit including a hospital information system (HIS), or a combination thereof.

Figure 1B:
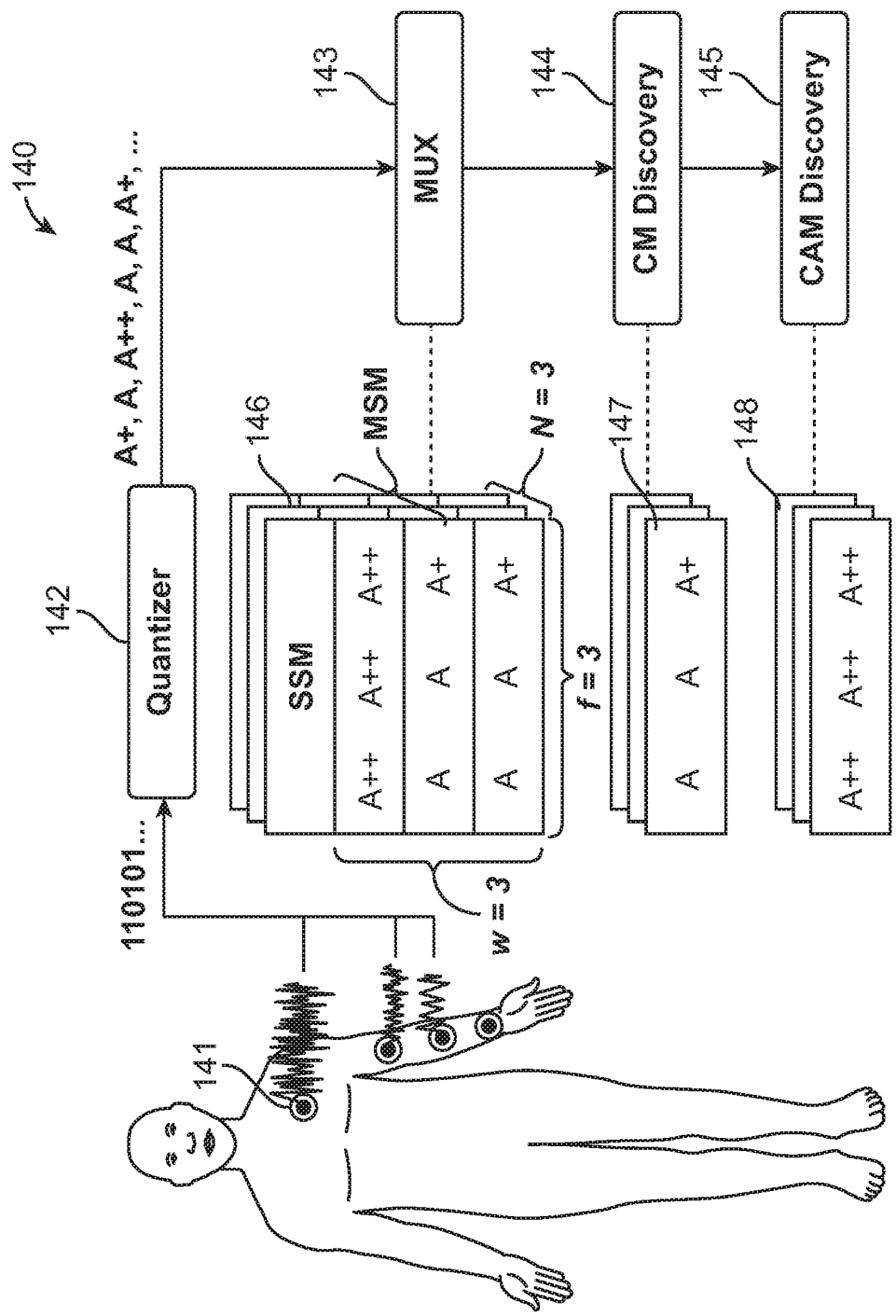
FIG. 1B shows a severity quantization technique that converts multi-sensor values to severity symbols.

In some embodiments, step 140 of method 100 includes determining severity through a severity quantization technique, as shown in FIG. 1B. The multi-sensor values obtained from the patient in 141 are converted to severity symbols based on a combination of sensor values, inter-sensor correlation, patient's historical data, doctors' inputs, inter-patient machine learning models among other factors. In various embodiments, the severity quantization includes sending the data to a data summarization and a detection module for patient data severity in 142. The module interprets a large amount of multi-sensor data and converts it to form sequence of severity symbols, called motifs that are arranged in a patient specific matrix as shown in FIG. 1B. In some embodiments, the module passes the quantized time series data to the MUX (multiplexer) in 143 as shown in FIG. 1B. In some embodiments, the MUX (multiplexer) arranges the quantized time series data into a three-dimensional multi-sensor matrix (MSM) consisting of multiple 2-dimensional single sensor matrices (SSM). In an SSM 146, the quantized values, say $A^*t, A^*t+1, A^*t+2$ etc. (where "*" represents severity values "+" or "++" or "−" or "−−", etc.), are arranged as increasing time series data in f columns and w rows, where f is the frequency of sensing and w is the observation window. Two different motifs are derived from any amount of large multi-sensor data (a) the most frequently occurring near normal trend in patients' data, called consensus normal motif (CM) as derived in 144, and (b) the most frequently occurring severe abnormality in the patient's data, called consensus abnormality motif (CAM) as derived in 145. In some embodiments, the method of identifying the motif is as illustrated in FIG. 1B, which compares individual data points in one sequence with other non-overlapping data points. In some embodiments, the comparison of individual data points is simplified as a quantized value $A^*t$ is compared with another value $A^*n$, where n is a multiple of a constant time separation that is called comparison interval, denoted as I.

In one embodiment, the method is configured to generate clinically relevant alerts based on an aggregate criticality score called the "Alert Measure Index" (AMI) that is calculated using available time for doctor's intervention.

In some embodiments the continuous values from the sensors are converted to K different discrete severity level symbols for differentiating the quantized values from actual real values of the sensor data. In some embodiments, the normal values are assigned the symbol A, while above-normal and subnormal values are quantized into A++, A+, A−, A−−, etc., respectively, according to varying severity levels. The + symbol representing the above normal and − symbol representing subnormal values. In some embodiments, it is assumed that different vitals have different number of severity levels.

Figure 1C:
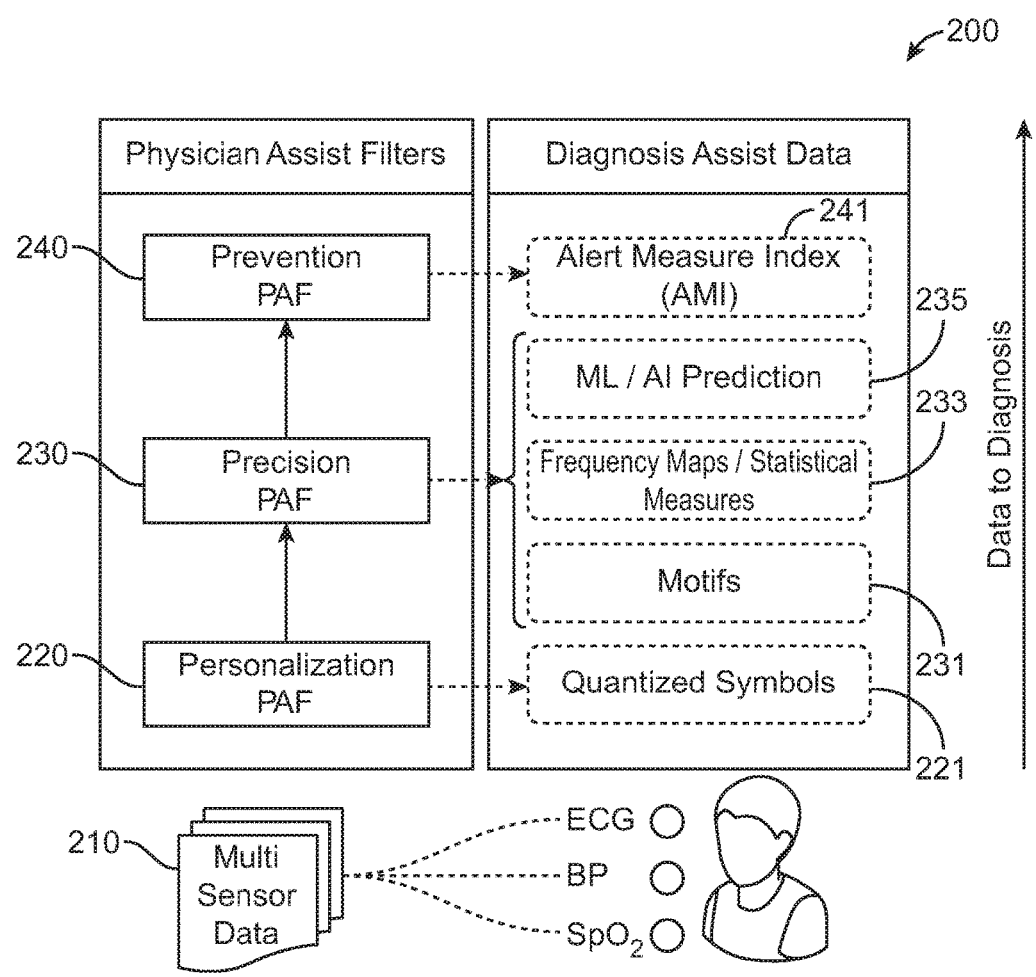
FIG. 1C shows PAF framework that progressively converts the raw multi-sensor data into quantized symbols, helpful motifs, diagnostic predictions and critical alerts.

In some embodiments, the method utilizes a physician assist filter (PAF) 200 as shown in FIG. 1C that includes a personalization PAF 220, a precision PAF 230 and a prevention PAF 240. The personalization PAF converts the multi-sensor values to quantized severity symbols 221 and stores it in a Patient Specific Matrix (PSM). The precision PAF 230 extracts consensus motifs 231, generates severity frequency maps (SFMs) 233 and includes a machine learning algorithm (ML) 235 that may diagnose the abnormality in a patient. The PAF further includes a prevention PAF that may generate an "Alert Measure Index" (AMI) 241 of the abnormality detected.

In various embodiments the quantized severity symbols are personalized for each patient through the personalization PAF 220. The quantized severity symbols are arranged into a Patient Specific Matrix (PSM) of N rows and W columns, where N is the total number of sensors being observed, and W is a time window in which the data is summarized. The value of W can be set by a physician or automatically derived based on the risk perception of that particular patient.

In some embodiments, precision PAF 230 includes extracting a Candidate Motif, μCNM [P] that is a temporally ordered sequence of quantized consensus normal symbols belonging to N rows that are selected from PSM of patient P. In some embodiments, a Consensus Normal Motif, μCNM [P] a candidate motif in which all values represent the normal severity level $\alpha_{NORM}$, that means each and every value, is equal to A is determined. α[p] includes the p-th quantized severity symbol in a row of the PSM, α[1], α[2], . . . , α[p], . . . , α[W]. In some embodiments the observation window of the PSM includes candidates C represented by $$C=\{\alpha[1],\alpha[2],\ldots\alpha[p],\ldots\alpha[W]\} \quad (1)$$

μCNM[P] is represented as:

$$\mu_{CNM}=\alpha_{CNS}[C_1],\alpha_{CNS}[C_2],\ldots\alpha_{CNS}[C_N]> \quad (2)$$

where $\alpha_{CNS}[C_1]$, $\alpha_{CNS}[C_2]$, . . . $\alpha_{CNS}[C_N]$ represent consensus normal symbols.

In some embodiments, a Consensus Motif (CM) 144, μCNM[P] a candidate motif satisfying the following two conditions: its hamming distance from μNOR[n] does not exceed a physician prescribed sensor-specific near normality bound, dNOR[n] and, its total Hamming distance D(α[p], $\alpha_{NORM}$) from all other μCAN[n] is the minimum. μCON represents the observed patient-specific near normal trend, is determined. The consensus normal symbol is represented as $$\alpha_{CNS}[C_p] = \begin{Bmatrix} \alpha[p]:D(\alpha[p],\alpha_{NORM})<S[n]_{THRESH} \\ \sigma[p] is the lowest such candidate \in H \end{Bmatrix} \quad (3)$$

where $S[n]_{THRESH}$ is the near-normal severity threshold.

$$\sigma[p]=\Sigma_{i=1}^{W}D(\alpha(p),\alpha(i)) \quad (4)$$

where α[p] denotes the sum of Hamming distances of α(p) from α(i).

In some embodiments, a Consensus Abnormality Motif (CAM) 145, μCAM[P], a candidate motif satisfying the following two conditions: its hamming distance from $\alpha_{NORM}$ exceeds a physician prescribed sensor-specific near normality bound, dNOR[n] and, its total hamming distance from all other μCAN[n] is the minimum is determined. μCAM[P] is represented as $$\mu_{CAM}=\alpha_{CAS}[C_1],\alpha_{CAS}[C_2],\ldots\alpha_{CAS}[C_N]> \quad (5)$$

where $\alpha_{CAS}[C_1]$, $\alpha_{CAS}[C_2]$, . . . $\alpha_{CAS}[C_N]$ represents consensus abnormality symbol and wherein $$\alpha_{CAS}[C_p] = \begin{Bmatrix} \alpha[p]:D(\alpha[p],\alpha_{NORM})\geq S[n]_{THRESH} \\ \sigma[p] is the lowest such candidate \in H \end{Bmatrix} \quad (6)$$

In one embodiment, the prevention PAF generates an alert measure index (AMI) based on the severity level of the patient's abnormality. The AMI score may prioritize the patient The AMI is calculated as:

$$AMI[P]=\Sigma_{n=1}^{N}\theta[S_n][\mu_{CAM}[P][n]*num(\mu_{CAM}[P][n])] \quad (7)$$

where $$\theta[S_n][\alpha]=\frac{K_1}{\Delta[\alpha]}$$

is a sensor and severity symbol-indexed matrix of weights derived using interventional time, Δ[α] is intervention time and α is severity level.

Figure 1D:
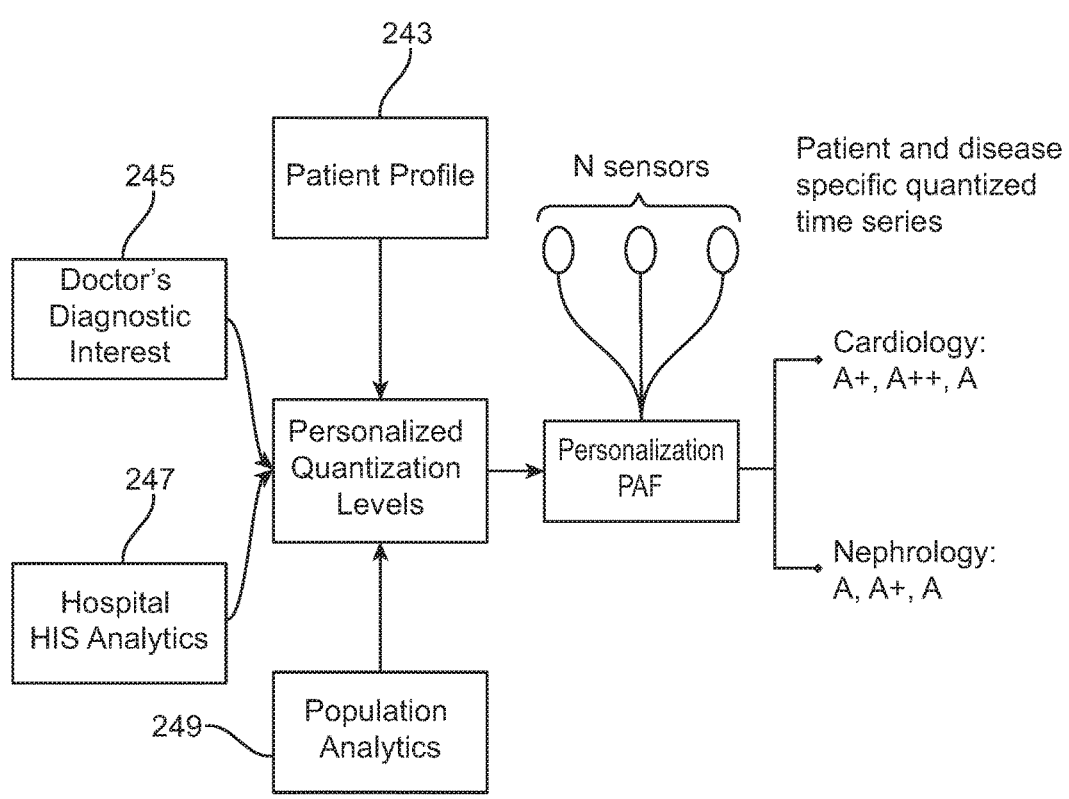
FIG. 1D illustrates quantization of sensor data based on multiple severity categorization criteria, resulting in the generation of patient and disease specific quantized values.

In one embodiment the quantization of sensor data as shown in FIG. 1D is based on multiple severity categorization criteria, resulting in the generation of patient and disease specific quantized values. In various embodiments, the multiple severity categorization criteria may be patient profile 243, doctor's diagnostic interest 245, hospital HIS analytics 247, population analytics 249. In some embodiments, the method includes connecting to the remote PAS, such as a cloud PAS. In some embodiments, the system can use a hybrid of ad hoc and infrastructure methods to connect to one or more of cloud PAS, the body-worn device or the mobile computing device. In other embodiments, when the infrastructure connectivity through mobile data network or Wi-Fi is unavailable, the mobile computing device can connect to other nearby mobile computing device in an ad hoc manner to deliver the data to the cloud PAS.

In various embodiments of the methods for use in the system, Health Service Personnel (HSP) access the data provided by cloud PAS or HIS PAS using web or mobile applications. In one embodiment, the HSP may include one or more of doctors, nurses, technicians, or emergency responders who analyze the data and take necessary steps. In some embodiments, emergency responders are configured to use the most reliable SoS communication channel from the available ones while responding to any contingencies.

In various embodiments, the methods implemented in the system provide mechanisms to analyze the sensor data coming from data aggregation and transmission unit to mobile computing device to conclude the usability of data. In some embodiments, methods to autocorrect data or retrieve error-free data using signal-processing techniques are also included. In certain embodiments, the method is a method of automatic detection of lead reversal in ECG signals and auto-correction.

Figure 2:
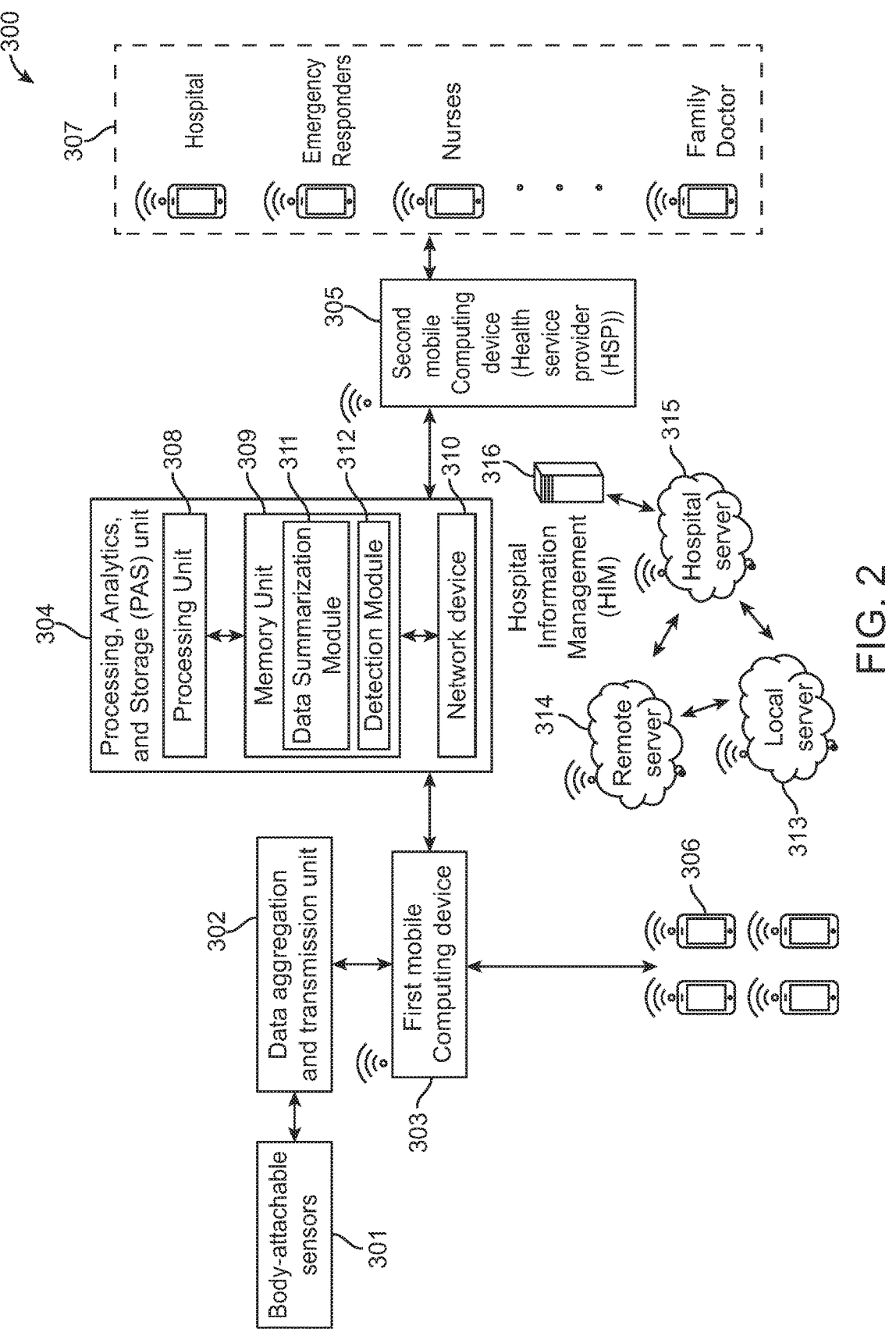
FIG. 2 shows a system for remote monitoring of a patient.

In various embodiments a system 300 for use in remote monitoring of a patient is disclosed. The system 300 as shown in FIG. 2 includes at least one sensor unit 301 attached to the patient's body to obtain sensor data of various health parameters, a data aggregation and transmission unit 302 that is interfaced with sensor unit 301 to receive the sensor data, a first mobile computing device 303 that is configured to receive and transmit the sensor data through a wireless communication network, at least one processing, analytics and storage (PAS) unit 304 that is configured to receive, analyze and store the sensor data from the first mobile computing device. In some embodiments the first mobile computing device 303, the PAS unit 304, or a combination thereof is configured to detect one or more abnormality in the sensor data, quantize a severity and identify if quantized severity exceeds a severity threshold. The system 300 further includes a second mobile computing device 305 that receives data from the PAS 304 and that may notify a Health Service Provider (HSP) in case of any severity exceeding the severity threshold. In various embodiments the data aggregation and transmission unit 302 is configured to notify the first 303 and/or the second 305 mobile computing devices when the quantized severity exceeds the severity threshold. In some embodiments the severity threshold for the patient is based on sensor data, inter-sensor correlation, patient's historical data, doctor's inputs, inter-patient machine learning models, or a combination thereof.

In some embodiments, the sensor unit 301 includes body attachable sensors for obtaining sensor data from physiological signal measurements. The sensor unit 301 may include at least one of a BP sensor that could measure the blood pressure level of the patient, a glucose sensor to sense the concentration of glucose in blood, a SpO2 sensor to measure the oxygen saturation level in a patient's hemoglobin, an ECG sensor that records the electrical activity of the heart, a motion detection system, an accelerometer or a GPRS.

In some embodiments, the systems and other components in FIG. 2 may be computing devices, such as servers, desktop computers, laptop computers, tablet computers, personal digital assistants (PDA), smartphones, mobile phones, smart devices, appliances, sensors, or the like. The computing devices may include processing units, memory units, network interfaces, peripheral interfaces, and the like. Some or all of the components may comprise or reside on separate computing devices or on the same computing device. In some embodiments, the devices may be configured to utilize various communication protocols, such as Global System for Mobile Communications (GSM), General Packet Radio Services (GPRS), Enhanced Data GSM Environment (EDGE), Code Division Multiple Access (CDMA), Wideband Code Division Multiple Access (WCDMA), Bluetooth, High Speed Packet Access (HSPA), Long Term Evolution (LTE), 5G, 5G-New Radio, and Worldwide Interoperability for Microwave Access (WiMAX).

In one embodiment, the first mobile computing device 303 is configured to transmit the sensor data through a GSM, 2G, 3G, 4G, LTE, Wi-Fi network or an Ad-hoc network created with neighboring wireless terminals or devices 306. In some embodiments the second mobile device 305 is configured to connect to other mobile devices 307. Mobile devices 307 may be associated with other health service personnel such as specialist practitioners, emergency responders, technicians, nurses, caregivers, and hospital administrators.

In various embodiments, each PAS unit 304 may be a computing device including at least a processing unit 308, memory unit 309, and/or network device 310. The memory unit 309 may include a data summarization module 311 and/or detection module 312. The data summarization module 311 may be configured to interpret a large amount of multi-sensor data and convert the data to form sequence of severity symbols or motifs. The severity symbols may be converted such that they are arranged in a patient specific matrix. In one embodiment, the system may include more than one PAS unit 304 with processing, analytics, and storing capabilities. For instance, the system may include multiple servers as PAS units 304, such as a local server 313, a remote server 314 and/or a hospital server 315 connected by a wired or a wireless network. In one embodiment, the hospital server includes a hospital information management (HIM) system 316. In various embodiments, the data aggregation and transmission unit 302 is interfaced with sensor unit 301 to receive the sensor data. The interfacing of the unit 302 with the sensor unit 301 could be either through wired or wireless connections. In some embodiments, the data aggregation and transmission unit 302 is a wearable device such as body-worn, small-form factor data collection, caching and/or dissemination unit that is connected to body sensors through a collection of wired and wireless media, for prolonged remote real-time monitoring of patients and/or in-ward telemetry.

In one embodiment, the system includes a mobile computing device 303 to receive, store, process, visualize, analyze and forward the data sent from the data aggregation and transmission unit. In some embodiments, the system additionally includes an application running on the device 303 for collecting location information of the user and the accelerometer reading from the device 303.

In various embodiments, the PAS unit 304 optionally includes one or more servers 313, 314, 315 and 316 that can receive, store, process, analyze and push data to mobile terminal 303 or 305 and associated application, which can visualize and present patient health status to doctors, hospitals, caregivers and emergency responders based on the criticality of the data. In various embodiments, the PAS 304 is a local PAS module 308 based on a simpler algorithm for initial analysis and early warning dissemination of data. The local PAS 304 in some embodiments can also use the APIs provided by the cloud PAS to do complex PAS tasks and is connected over an existing infrastructure. In some embodiments, the mobile computing device 303, 305 or data aggregation and transmission unit 304 may also be integrated with a PAS module that incorporates PAS algorithms that may run as background services in the smartphone itself. In one embodiment, the system includes a complex PAS Layer that implements disease detection, big data analytics, complex storage policies and computationally intensive algorithms that are not possible to be implemented in local PAS due to its processing and power constraints. In various embodiments, the complex PAS is implemented through a remote server 313 or through a hospital server 315, or could be local to the hospital server such as a HIM 316. In some embodiments, hospitals might have different policies on patient data storage and processing. In these embodiments, a centralized storage and processing policy may not be used, and the hospitals may access the services provided by the cloud PAS through APIs over existing infrastructure.

In some embodiments the data aggregation and transmission unit 302 includes one or more of a rechargeable body-worn hardware unit, sensors such as ECG, BP, SpO2, blood glucose sensors attached to the body and interfaced with the data aggregation and transmission unit over wired or wireless media. In some embodiments, the data aggregation and transmission unit 302 can continuously record sensor data and is configured to capture asymptomatic episodes of patient disease. In some embodiments, the data aggregation and transmission unit 302 is configured to tag sensor data as related to physiological symptoms using a button in the data aggregation and transmission unit. In some embodiments, the data aggregation and transmission unit 302 is configured to use voice-based tagging of data in the smartphone which allows patients to speak about an event, which is tagged along with the sensor data. In some embodiments, the voice-based tagging of data allows the patients to make specific complaints related to the event. In some embodiments, the data aggregation and transmission unit 302 is configured to send a SoS signal to the healthcare personnel in case of emergency conditions. In some embodiments, a motion detection system including an accelerometer is placed inside the data aggregation and transmission unit. In certain embodiments, the data aggregation and transmission unit 302 is connected to the patient's smartphone over a wireless network to transmit the raw data. In some embodiments, the data aggregation and transmission unit 302 is connected to the patient's smartphone over a short-range wireless network. In some embodiments, the smartphone has applications related to data analysis and processing. In some embodiments, the data aggregation and transmission unit 302 can also include an in-built GPRS module that can directly send data to the remote healthcare personnel's smartphone or a remote data reception unit.

In various embodiments, the sensors send the data to the data aggregation and transmission unit 302. The data aggregation and transmission unit 302 then forwards the data to the patient's smartphone or another mobile computing device 303 configured to perform computation and real-time processing. There can be multiple devices in the neighborhood 306. These devices can have varying capabilities and can be linked over a heterogeneous network, such as WiFi or Bluetooth. The patient's handheld device can also be connected to another patient or health service personnel (HSP), such as that of a doctor or a clinician. The handheld devices are connected to a server, such as a private or public server over different media and networks. In some embodiments, the server may be a cloud based server. The cloud has higher capabilities for batch processing than the handheld devices as well as large storage space for long term archival of data. The public and private parts of the cloud are also connected through proper interfaces.

In various embodiments, the data aggregation and transmission unit 302 and mobile computing device 303 are configured to communicate with each other and share their processing and storage capabilities, independent of the cloud PAS. In some embodiments, the patient's data is routed to the doctors' handheld device skipping the cloud PAS, thereby reducing the upstream traffic to the cloud PAS. In certain embodiments, the data archival in the cloud PAS is done later when the cost of transmission is lower. In these embodiments, the system architecture allows the handheld devices to go offline from the cloud PAS and then join in later through a different network.

Figure 3:
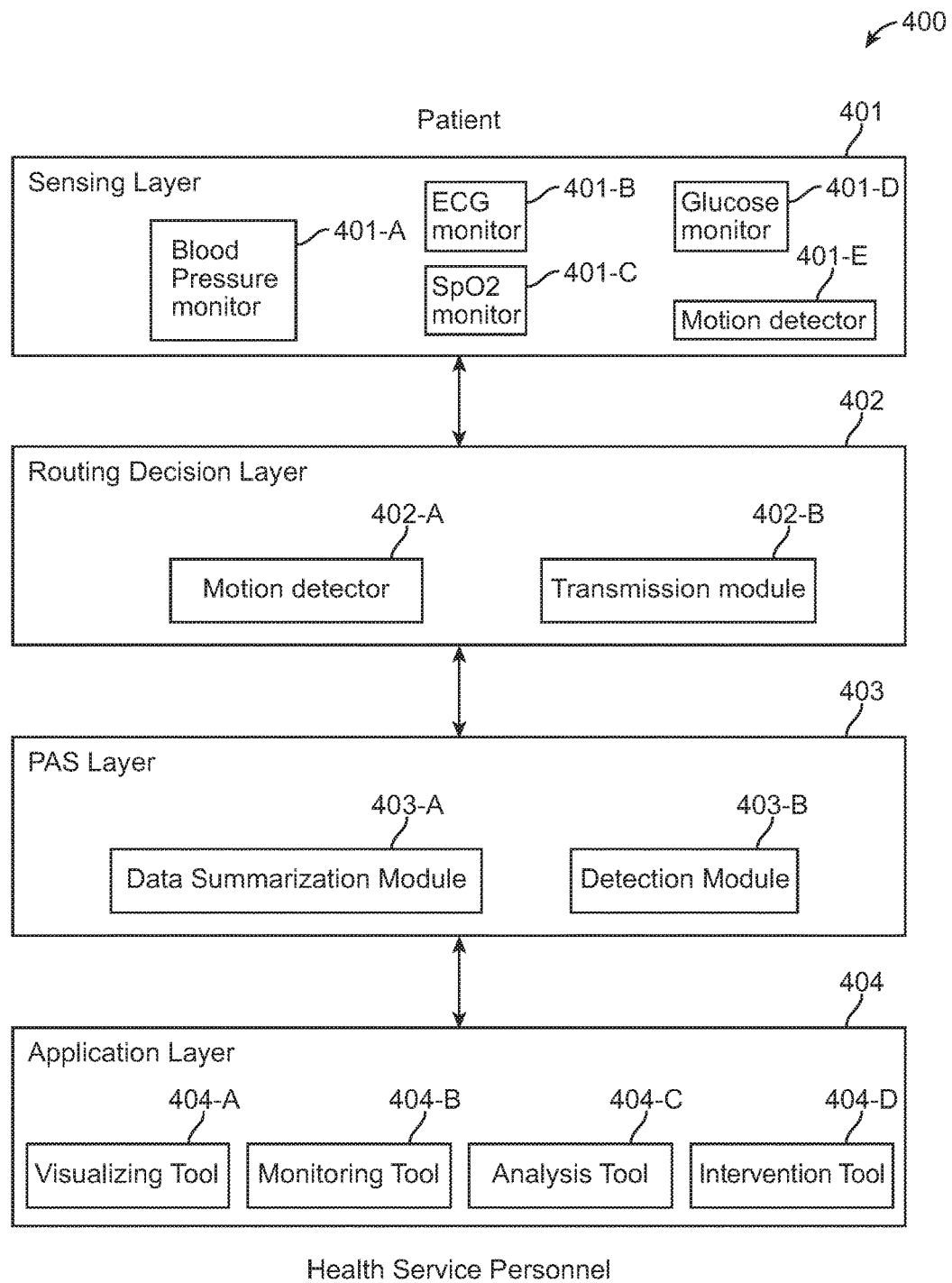
FIG. 3 shows a multilayer system communication and analytics architecture.

In various embodiments, the remote health monitoring system 300 of the invention includes architecture 400 as illustrated in FIG. 3. The architecture 400 may include one or more layers for performing the method 100. The layers include a sensing layer 401, a routing decision layer 402, a PAS layer 403 and an application layer 404. In some embodiments, the sensing layer 401 includes sensor modules for continuously monitoring at least one or more of sensors connected to the patient's body such as BP 401-A, ECG 401-B, SpO2 401-C, and glucose 401-D, as well as the user activity such as by using accelerometer motion detector 401-E. In some embodiments, the routing decision layer includes a data aggregator 402-A and transmission module 402-B. In some embodiments, both data aggregation and transmission is performed by a single unit such as a body-worn device connected over a short-range wireless network. The unit receives data from the sensors 401 and directly sends it to a first mobile computing device. In some embodiments, the Routing Decision Layer 402 performs three functionalities: a) to decide where and when the sensed data needs to be processed, analyzed and stored b) to decide the best routing path out of the available heterogeneous options c) to interface and exchange data with the nearby mobile device or data aggregation and transmission unit over ad hoc networks. The PAS layer includes data summarization module 403-A and patient data severity detection module 403-B that interprets a large amount of multi-sensor data and converts it to form sequence of severity symbols for subsequent processing. The application layer 404 in various embodiments includes various visual tool 404-A, monitor tool 404-B, analysis tool 404-C and intervention tool 404-D. Users of the second mobile device, such as hospitals, medical practitioners, nurses, etc., may be provided a graphical user interface in the application layer. The users may perform various actions including monitoring, analyzing, and intervening using the mobile device. In some embodiments, a wired Ethernet using existing hospital infrastructure connectivity is also utilized alternatively.

Figure 4:
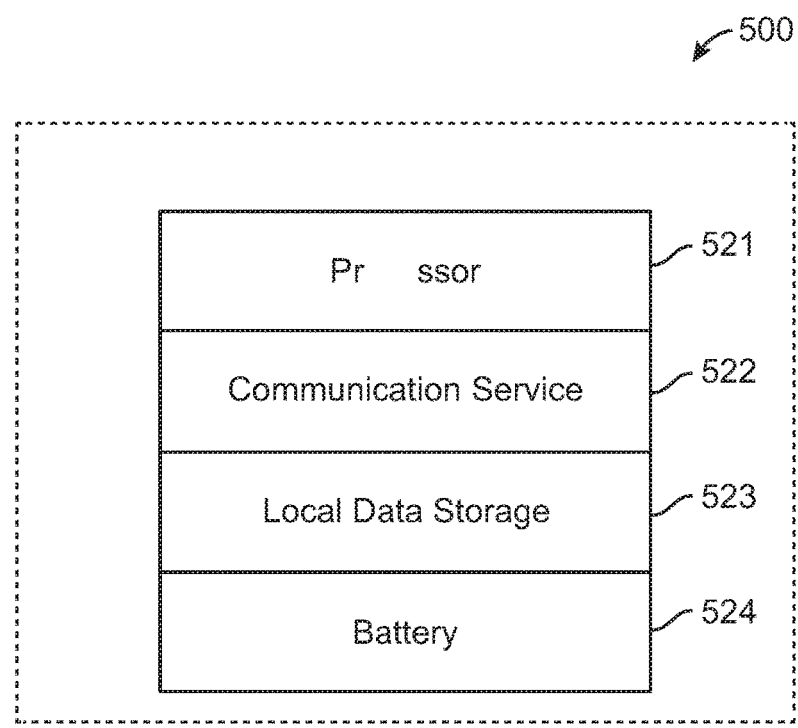
FIG. 4 shows a body-worn device for use in a system for prolonged remote real-time monitoring of a patient.
Figure 5A:
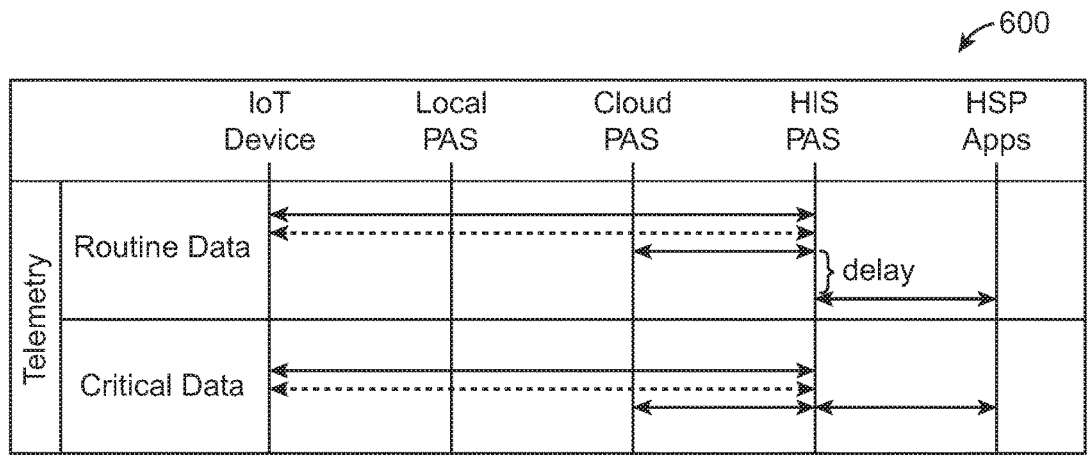
FIG. 5A shows a heterogeneous path selection mechanism for patients who are inside the hospitals, such as in-ward telemetry.
Figure 5B:
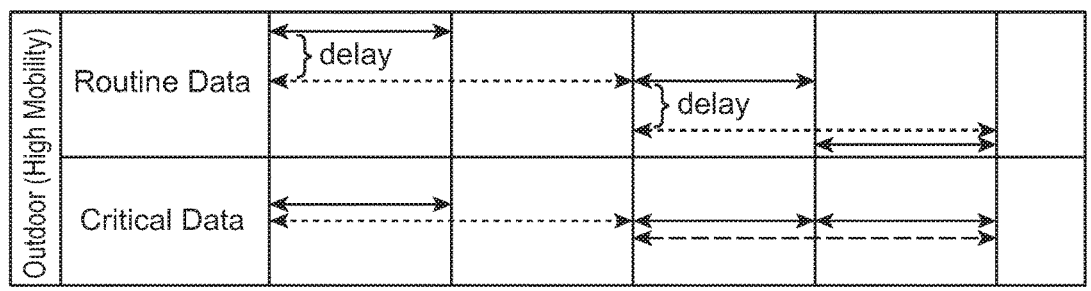
FIG. 5B shows a heterogeneous path selection mechanism for high mobility patients who are outdoor.
Figure 5C:
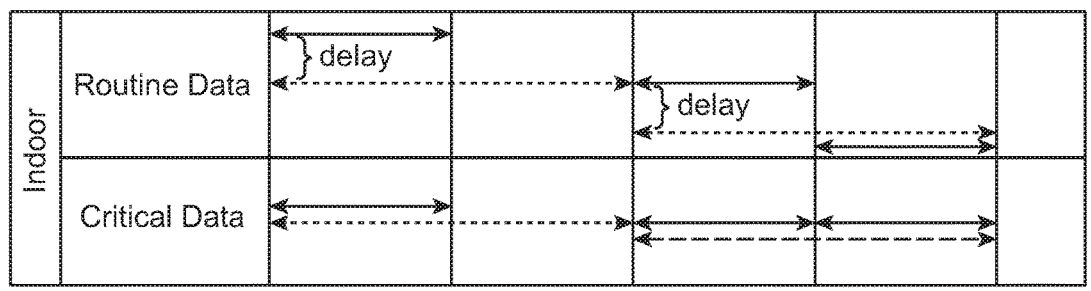
FIG. 5C shows a heterogeneous path selection mechanism for patients who are indoor.

In various embodiments the data aggregation and transmission unit 302 for prolonged remote real-time monitoring of a patient is a body-worn device 500 as shown in FIG. 4. The body-worn device 500 includes at least one processor 521 configured to calculate MP-CAM and AMI, a wireless communication module 522, a memory or data storage module 523, and a power supply unit or battery 524. The device 500 is configured to receive inputs from the one or more body sensors 301 through wired or wireless connections. In some embodiments, the device 500 includes a hardware switch that may tag the received sensor data to related physiological symptoms. The device 500 may further include a motion detection system that includes an accelerometer. The memory module 523 is configured to aggregate data received from the one or more sensors 301. The wireless communication module 522 is configured to transmit the data to at least one of a remote server 314, or a mobile device 305. In some embodiments, the device 500 includes a built-in power management system to prolong the available life of the battery 524. In one embodiment, the system includes prioritizing the communication-based on a mechanism 600 as illustrated in FIG. 5A, FIG. 5B and FIG. 5C that considers a combination of user location using GPS or other localization techniques, mobility data via smartphone sensors, and health criticality of the patient to prioritize communication. Accordingly, in some embodiments, prioritizing mechanism 600 may send critical data via a higher priority channel such as a direct link or a cellular GSM. In some embodiments, the mechanism sends routine data using any available channel with a delay to minimize congestion or optimize bandwidth availability or both.

In various embodiments of the systems and methods disclosed herein, a reliable, low delay tolerant communication network is provided. The systems and methods envisage providing optimal network support in rural regions, where availability and reliability of networks is a challenge. In other embodiments, in urban settlements, methods such as selecting the least cost network, ensuring continuous bandwidth availability, etc., can also be incorporated. In case of highly mobile patients, the methods in some embodiments are configured to take into account frequent change in mobile base stations. In some embodiments, in addition to the above considerations, health data priority and patient context may also be used to optimize route selection.

In various embodiments, the priority of the data is determined from the type of sensing and the analysis results from local PAS. In some embodiments, two data priority levels, 1) routine data and 2) critical data are determined. In various embodiments, routine data is collected during routine sensing and acquisition scenario. In some embodiments, the routine data is sent to the local PAS if available from the mobile computing device or data aggregation and transmission unit, and the method envisages classifying the data as routine or critical. In one embodiment, based on the result of local analytics, if the vital measurement shows variations from normal level, it is tagged as critical. In another embodiment, if the data does not show any significant variations, it is stored in the mobile computing device or data aggregation and transmission unit cache and transmitted at a later time over a non-time critical path. In some embodiments, if the mobile computing device or data aggregation and transmission unit do not have connectivity to a local PAS, they transmit the data to the complex PAS layer. In embodiments where the data is classified as routine data and therefore not of immediate use by the HSP, a delayed transmission through non-time critical route is adopted and the routine data is accessed by the HSP at a later point of time.

In some embodiments, the data is classified as critical data if it consists of data collected during patient or doctor triggered sensing. In some embodiments, the method includes sending the data to the local PAS and analyzing for any deviations from normal values before deciding the routing path. In some embodiments, in the absence of a conclusive result from the local PAS (or even non-availability of local PAS), the data is transmitted to the complex PAS through a time-critical route and then notified to the HSP immediately in order to help them make emergency interventions.

In some embodiments, the system includes use of one or more applications of remote health services for patients who are inside the hospitals, such as in-ward telemetry as shown in FIG. 5A when a patient needs to be monitored after a critical operation. In some embodiments, the system includes monitoring patients who are discharged from the ICUs to general ward by a HSP. In some embodiments, the mobile computing device or data aggregation and transmission unit communicates with the existing hospital infrastructure using Wi-Fi or wired Ethernet connection. In some embodiments, a reliable low-cost route to reach the HIS PAS is utilized and the mobile computing device or data aggregation and transmission unit need not send the data to a local PAS. In other embodiments, a communication framework which is able to deliver all the services through a highly reliable, high bandwidth WiFi or direct link connection is provided. In some embodiments, the HIS PAS may communicate with the cloud PAS through APIs for various needs through a high bandwidth link, which is part of an existing infrastructure. In other embodiments, an indoor routing policy is adopted in the absence of a reliable hospital infrastructure.

In some embodiments, the monitoring is outdoor monitoring as shown in FIG. 5B. In certain embodiments, the system includes transmitting the data to the cloud PAS based on the data priority from the mobile computing device or data aggregation and transmission unit. In some embodiments, a combination of cellular data and Wi-Fi are used when selecting a time critical route, if the mobility pattern is already known. In alternate embodiments, a route based on GSM is used when selecting in the absence of a known pattern. In some embodiments, the transmission of routine data is delayed till the device reaches an indoor environment from the mobile computing device or data aggregation and transmission unit. In other embodiments, the mobile computing device or data aggregation and transmission unit can opt to search for an IoT gateway over an ad hoc network.

In some embodiments, the monitoring is indoor monitoring as shown in FIG. 5C. In certain embodiments the framework includes routing policy assumes that the issues of switching cellular base stations and WiFi networks does not arise as much compared to an outdoor location. In some embodiments, the routing path is decided from the results generated in the local PAS by forwarding the data from a mobile computing device or data aggregation and transmission unit. In some embodiments, the data is transmitted over Wi-Fi or cellular data network, even in critical situations and a GSM based route is not required unless other options are unavailable. In some embodiments, the mobile computing device or data aggregation and transmission unit can form ad hoc network with other mobile computing device or data aggregation and transmission unit and send the data through the gateway device in the absence of an infrastructure to access internet.

In sensor networks, power is a major consideration to decide the frequency of sensing, data processing, route selection and transmission frequency. In some embodiments of the invention, the architecture allows taking these decisions at both the mobile computing device and data aggregation and transmission unit.

In some embodiments, the framework includes defining a power policy 700 defined based on the different levels of available battery power, as illustrated in FIG. 5D. In some embodiments, the devices are usually attached to or near the user and the devices are recharged at least once in a day if required.

In some embodiments, each sensor has different sensing frequencies. In one embodiment, the method includes measuring BP and blood glucose only twice or thrice in a day. In some embodiments, the patient is on continuous ECG monitoring and the sensor transmits the data continuously. In some embodiments, there is difference between the sensing and transmission energy requirements for different sensors. In additional embodiments, the method includes defining the available battery power of devices and sensors as the time up to which it can carry out of sensing and transmission. In some embodiments, the absolute values given can be altered according to different usage scenarios using a power management mechanism based on available battery power, the data priority and location of the patient.

In some embodiments, the system includes defining the available power as low, medium and high as shown in FIG. 5D. In some embodiments the available power is defined as low, when there is only enough battery power to sense and transmit for below three hours. In other embodiments, the device has to be recharged within a specified time, to ensure continuous sensing and data availability. In some embodiments, the available power is defined as medium, when there is enough battery power to support sensing and transmission between 3-12 hours. In some embodiments, the available power is defined as high, when there is enough battery power to support sensing and transmission between 12-24 hours.

In certain embodiments, the system includes a framework capable of immediately transmitting the data (specified as "Immediate"). In some embodiments, the method includes a framework capable of storing and sending (specified as "Delayed") at a later point of time, when the battery level improves. In yet other embodiments, the method includes a framework capable of sending the data to the local PAS for processing (specified as "Local PAS"). In some embodiments, the delayed transmission results in conserving available resources while the Immediate and local PAS results in higher battery drain. In some embodiments, it is assumed that the power requirements for local PAS is much less compared to the transmission cost to the cloud PAS.

In some embodiments, network selection plays an influential role in the context of power management. In some embodiments, the transmission power for different media varies. In some embodiments, the power management policy is to select the least power-consuming medium. In other embodiments, the health context of the patient also needs to be factored in. In some embodiments, the power management policy includes a three-level decision mechanism that includes selecting a subset of paths based on the routing policy, deciding on processing, transmission, and storage based on the battery level, and choosing from one or more medium options for transmission, the medium with the least power requirements.

In one embodiment, the routing and power policies are firmly based on reliable delivery of relevant health data to the HSPs. In some embodiments, the routing and power policies are based on the patient context, which includes his health status, activity and location, to dictate which path to be taken and when the data needs to be transmitted. In one embodiment, the critical data is always transmitted, while routine data is transmitted at a later time. In another embodiment, the path selection is based on power policy and location and results in conserving battery.

In some embodiments, a sensor signal quality analyzer is included to detect if the sensor signal received is usable data. In other embodiments, an auto-correction algorithm is included to retrieve the original signal from the unusable signal for correction of human errors such as lead misplacement in ECG signals. In some embodiments, a patient feedback system that provides automated feedback to the patient regarding signal quality and suggestions to improve by changing the placement of the sensors or adjusting other physical parameters of the body sensors is included. In some embodiments, a primary patient condition analysis based on thresholds of the sensor signals that can tag the data as critical, non-critical or of unknown-criticality is included. In some embodiments, a data compression and storage mechanism for temporary storage of data in the smartphone is included. In other embodiments, a data transmission mechanism to send data to the healthcare personnel and the cloud is included. In one embodiment, an algorithm to decide the data transmission based on the availability of the mobile and data networks, cost of transmission, the power availability in the device and the criticality of data is included. In another embodiment, the mobile computing device includes a data visualization mechanism whereby the patient or caretaker can see the sensor data received in real-time on the smartphone.

In one embodiment, the method includes voice tagging of medically relevant physiological conditions or events. In one embodiment, a patient can tag the data using the button provided in the data aggregation and transmission unit or mobile computing device voice tagging capability using the microphone and using a user trigger in the device. In one embodiment, the method includes running a background service that constantly reads data from the data aggregation and transmission unit. In some embodiments, the method includes configuring the data aggregation and transmission unit using the smartphone. In other embodiments, the method includes visualizing various parameters of the data aggregation and transmission unit such as battery status and connectivity of body sensors.

In some embodiments, the system includes a decision support system (DSS) to detect abnormalities in sensor data used for prognosis and decision support for the HSP. In one embodiment, the system includes a DSS based on the capabilities of a mobile computing device and PAS. In other embodiments, preliminary DSS algorithms run on the mobile computing device while more complex DSS algorithms run on the PAS unit, such as a remote cloud server. In some embodiments, the system is configured to transmit the results of the DSS to the smartphone of HSP using the mobile computing device or PAS. In other embodiments, the system is configured to send alerts to the smartphone of HSP based on the severity of DSS results using SMS or GSM network along with cellular data or internet.

In some embodiments, the wearable device is configured to intimate relatives, HSP, or both in case of an emergency. In some embodiments, the method includes capturing of ECG, blood pressure, blood glucose, pulse rate, blood oxygen, and other vital parameters, and recording of data following a distress in patient as well as relatives, HSP, or both of the patient condition. In some embodiments, the method includes a SoS protocol for communication between the data aggregation and transmission unit, mobile computing devices and PAS, wherein the mobile computing device will act as a gateway to send emergency signals to remote hospitals along with the location of the patient. In some embodiments, the system is configured to transmit live stream of vitals during emergencies using GSM network or internet.

In some embodiments, the system includes enhancing patient management through a collective decision-making process by utilizing doctors from multiple specialties who consider various physiological, pathological and other patient parameters and come to their own specific conclusions, which are then discussed to arrive at a patient management plan. In one embodiment, a cardiologist may set patient and disease specific quantization levels from a sensor. In some embodiments, the cardiologist sets the ST elevation or depression alert levels to identify emergency episodes of myocardial infarction in high-risk cardiac patients. In some embodiments, the alert levels are coupled with the context of the patient. In one embodiment, the threshold level is set lower in sedentary workers when compared to sport persons or high activity patients with higher threshold levels for emergency and early detection. In another embodiment, the BP, heart rate (HR) or SpO2 severity levels are set for identification of long-term trends in obstructive sleep apnea. In yet another embodiment, the HRV, RRV, and BP severity levels are defined differently for detection and tracking of chronic obstructive pulmonary disease (COPD).

In one embodiment, a neurologist sets a patient and disease specific quantization levels from a sensor. In some embodiments, the severity levels of BP and pulse rate are set as a combination to alert the practitioner of a discrepancy between BP and pulse rate for the occurrence of autonomic neuropathy, one of the major risks seen in epileptic patients. In one embodiment, if the difference between BP and pulse rate is not above a given threshold, the doctor may set the quantization level such that emergency alerts are sent to them. In another embodiment, an endocrinologist sets a patient and disease specific quantization levels from a sensor. In one embodiment, a continuous blood glucose monitoring in high-risk patients is adopted to avoid complications arising out of hypo and hyper-glycaemia. In one embodiment, the severity levels is set based on blood glucose measurements over a long time interval depending upon the risk of the patients to prevent fatal events.

In another embodiment, an obstetrician sets a patient and disease specific quantization levels from a sensor. In one embodiment, continuous monitoring of fetal heart rate, mother's blood pressure, or both is done for early detection of any complications in high-risk pregnancies, which pose a severe threat to the mother and the child. In one embodiment, the obstetrician sets the severity quantizer level according to the specific condition of the mother and the fetus.

In some embodiments, the individual practitioners set patient and disease specific quantization levels from sensors, which are different from each other. In yet other embodiments, all practitioners may set severity levels of vital parameters in the same way, while specialized sensor severity levels may differ based on the patient. In some embodiments, the system is configured to utilize a RASPRO summarization technique and the associated algorithms.

While the invention has been disclosed with reference to certain embodiments, it will be understood by those skilled in the art that various changes may be made, and equivalents may be substituted without departing from the scope of the invention. In addition, many modifications may be made to adapt to a particular situation or material the teachings of the invention without departing from its scope. Further, the examples to follow are not to be construed as limiting the scope of the invention which will be as delineated in the claims appended here.

EXAMPLES

Example 1

A Method for Determining CM and CAM

Using the comparison of individual data points as illustrated above, A*1 is compared with A*(1+I), A*(1+(2×I)) etc. In the problem of CM and CAM discovery in SSM, we assume I=f. The first row of sequences is compared with the other rows in a temporally ordered row wise comparison. To discover CM and CAM in SSM, a Hamming distance based algorithm was used as illustrated here:

```
Input: SSM
Initialize:
L = f; HammingDistMat = [0,0]W×W; dNOR [0]W×1; SumMat
[0]W×1; CM_Index = 0; CAM_Index = 0;
Procedure: FindHammingDistances
for i = 1 to W
for j = i to W
HammingDistMat [i, j] = HammingDist (SSM [i], SSM [j])
HammingDistMat [i, j] = HammingDistMat [j, i]
dNOR [i] = HammingDist (SSM [i], MNOR)
end for
end for
for i = 1 to W
SumMat [i] = sum (HammingDistMat [i, ...])
end for
Procedure: FindCM
for k = 1 to W
index = find_K-th_minimum (SumMat, k)
if (dNOR (index) ≤ α)
CM_Index = index
break
end if
end for
Procedure: FindCAM
for k = 1 to W
index = find_K-th_minimum (SumMat, k)
if (dNOR (index) ≥ α)
CM_Index = index
break
end if
end for
Output: CM = SSM (CM_Index); CAM = SSM (CAM_Index)
```

First, the hamming distance of each of the $M_{CAN}$s from each other is determined followed by calculating their sums. The resulting summation matrix (Summate) along with the $d_{nor}$ matrix is used to find CM and CAM. For CM discovery, only those MCANs with $d_{NOR}$ less than α are considered while for CAM discovery those above α are used. Finally, an iterative method to find the index of the MCAN with k-th minimum sum of hamming distances from SumMat gives the CM and CAM index in the SSM.

Example 2

A Severity Quantization Technique for Continuous ECG Monitoring

Figure 6A:
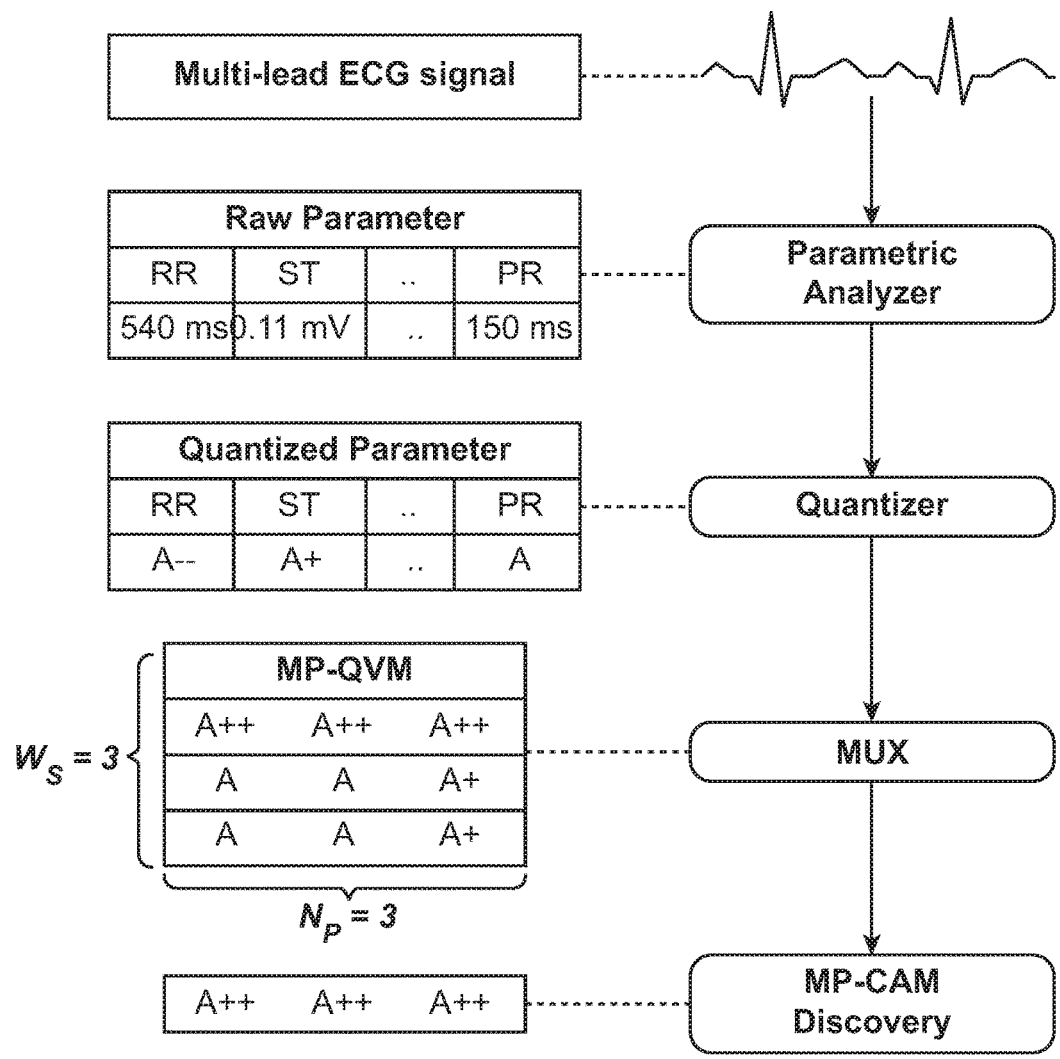
FIG. 6A shows a method of computing the Multi-Parameter Consensus Abnormality Motif (CAM) from raw sensor data.

A continuous monitoring ECG sensor as shown in FIG. 6A, SN is utilized. Suppose we intend to monitor a number of different parameters, P1, P2, Pi, such as RR interval, ST deviation, ST segment etc. Let us also assume that the total number of parameters is NP. The multi-parameter data is summarized and any criticality is identified such that a lucid report is sent to the doctors. Before abnormalities are found, the sensor data is preprocessed as follows.

First, the raw sensor data is processed by the parametric analyzer, which calculates the values of each parameter Pi, at a frequency of fP. Next, these parameter values are quantized into any of K severity symbols defined for the respective parameters (by the severity quantizer). The severity symbols are assigned as A+, A++, A-, A-- etc., based on the deviation from the medically accepted normal parameter value, which is denoted by the symbol A. The + and - symbols represent varying degrees of above-normal and subnormal severity levels. After this, the quantized values are sent to a mux, which constructs a multi-parameter quantized value matrix (MP-QVM). The columns of MP-QVM represent the different parameters, while the rows are time ordered quantized values. We describe a sample scenario below.

Suppose we need to discover a Multi-Parameter CAM (denoted as MP-CAM) once in every ten minutes, denoted as summarization frequency fS=1/600 (per sec). Assuming the parametric analyzer frequency fP=1 Hz, we discover CAM from an MP-QVM of 1/fS rows (denoted as observation window size WS) and NP columns. Next, the CAMs are discovered as discussed in the above section.

Interventional Time-Inverted Alerts: Alert Measure Index: At the end of each observation window Φr, in an SSM, for every patient, we define an aggregate alert score, called the Alert Measure Index (AMI). The AMI is derived from the severity symbols, combined with severity specific weights and sensor specific weights. One of the embodiments of this AMI could be modeled as below:

$$\text{AMI}[\Phi] = \Sigma_{i=1}^{N} W[i] * \Sigma_{j=1}^{F*1} \text{num}(\mu_{CAM}[i][j]) * \Theta[j] \quad (8)$$

Figure 6B:
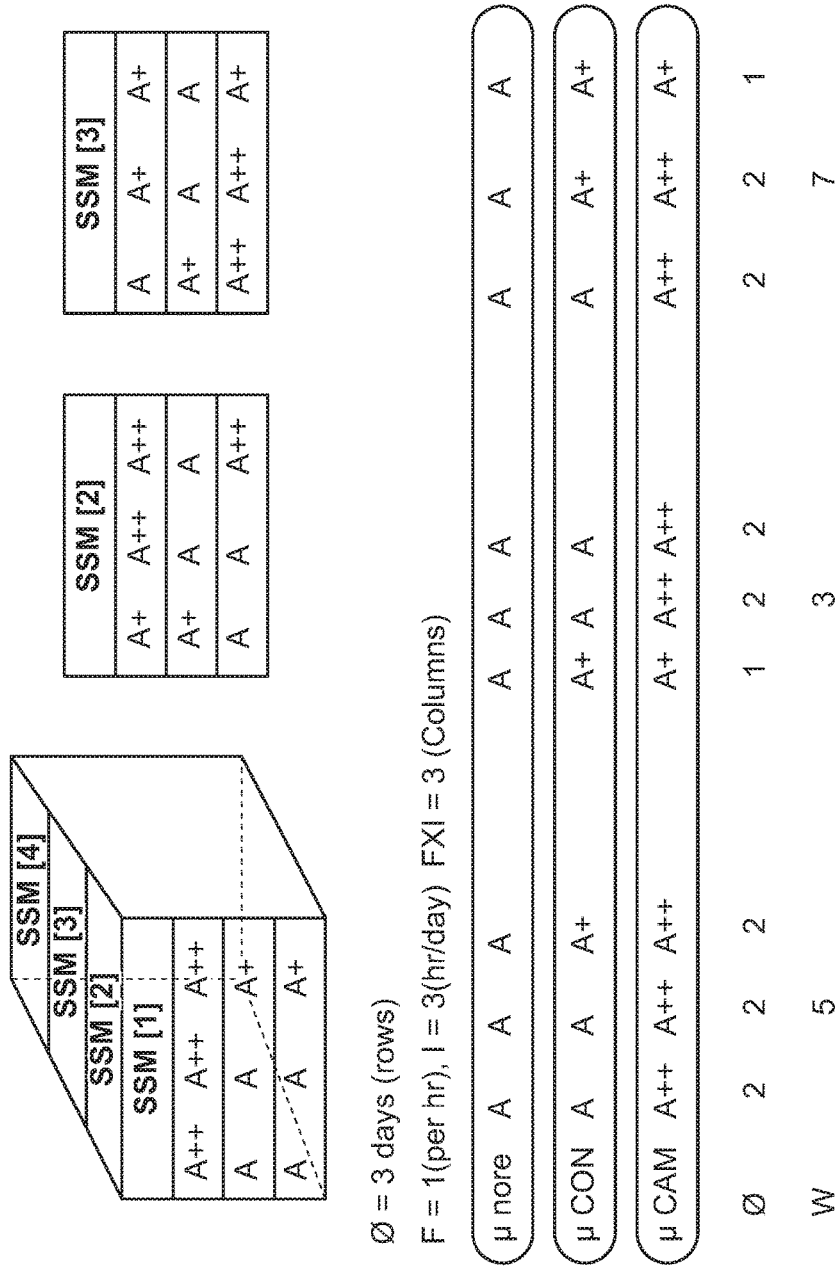
FIG. 6B shows a method of using Motifs to find the aggregate AMI score.

Wherein, the inner summation takes each severity value in the $\mu_{CAM}$ of the $i^{th}$ sensor, converts it into a numerical value (e.g., A± is assigned 1, A++/--α is assigned 2), scales it up by a severity specific factor Θ[j], and the outer summation scales it up by a sensor specific weightage W[i], both of which are derived from medical domain expertise, as illustrated in FIG. 6B. We call these two factors W and Θ as severity factors, and the resulting AMI is indicative of the immediacy of patient priority for physician's consultative attention.

We propose a goal directed approach to determining the severity factors W and Θ. The goal of delivering the alerts to the physician is to indicate the upper bound on the time that can elapse before which the physician's intervention is imperative to pull the patient out of danger. In order to capture this, we define the severity factors W and Θ as follows:

$$\Theta[\alpha] = \frac{K_1}{\Delta[\alpha]}, \; W[n] = K_2/\Delta[n] \quad (9)$$

where, $\Delta[\alpha]$ is the upper bound on the time for intervention for severity level $\alpha$ (which can take on values A++, A+, etc.), $\Delta[n]$ is the upper bound on the time for intervention for sensor n. In (2), constants K1 and K2 can be set by the physician considering the context of patient's health condition (including historical medical records and specific sensitivities and vulnerabilities documented therein). The inverse linear equation relating the severity factor to interventional time may be substituted with more complex equations for progressively complicated disease conditions. For instance, cardiologists prefer an exponential increase in alert levels if the monitored patient's ECG shows significant ST level depression: a direct indicator of myocardial infarction.

$$\Theta(\alpha) = e^{\wedge}((K_1/(\Delta(\alpha))))\quad(10)$$

AMI based frequency modulation: AMIs also serves as a feedback mechanism to modulate sensing frequency and alert computation instants. A low AMI is used to effect three adjustments: (1) Reduce the frequency F of future sensor measurements to a medically allowed minimum bound, (2) Increase the gap $\Gamma$ between successive monitoring intervals, and (3) Increase the subsequent inter-alert window $\Phi$, thereby saving power and bandwidth of transmission. Similarly, a high AMI causes F to increase, $\Gamma$ to decrease, and $\Phi$ to increase. One of the embodiments of this adaptive frequency modulation can be modeled as below:

$$F_{r+1} = F_r[1 + C1*(AMI(\Phi r) - AMI(\Phi r - 1))]\quad(11)$$

$$\Gamma_{r+1} = \Gamma_r[1 - C2*(AMI(\Phi r) - AMI(\Phi r - 1))]\quad(12)$$

$$\Phi_{r+1} = \Phi_r[1 - C3*(AMI(\Phi r) - AMI(\Phi r - 1))]\quad(13)$$

where, C1, C2, C3 are positive feedback constants adaptively set by physician's preferences. A very high frequency causes redundancy in summarization while a lower frequency may result in missing sudden short duration spikes in parameters. An optimum frequency has to be specific to the patient, sensor and severity.

Figure 6C:
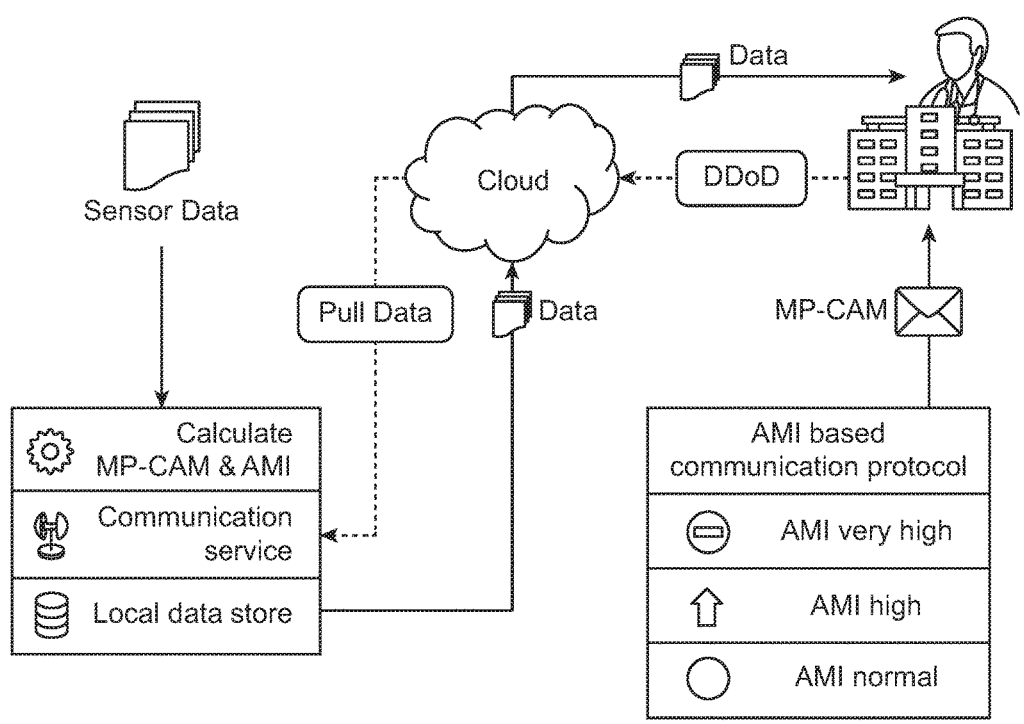
FIG. 6C illustrates a system and a method of calling data from the patient sensors according to perceived severity of the patient, through a technique called Detailed Data-on-Demand (DD-on-D).

Detailed Data on Demand (DD-on-D): Upon viewing the received AMI and CAM pertaining to a patient, the doctor may initiate a data pull mechanism, abbreviated as "DD-on-D" originating from the doctor's device to the cloud, as shown in FIG. 6C. The DD-on-D may further propagate to the patient's smartphone if part or whole of the data requested is still remnant on the patient's smartphone. The response to this request may trigger spontaneous switching on of the smartphone data if connectivity is available, and if not, refined summaries are transmitted via successive sequence of SMSs or MMSs. The DD-on-D also handles other data related directives from the doctor, such as a request to increment (or decrement) the summarization frequency, so that he/she receives CAMs more (or less) often from that particular patient.

Example 3

A System for Remote Monitoring of Vital Parameters in Patients

Figure 7:
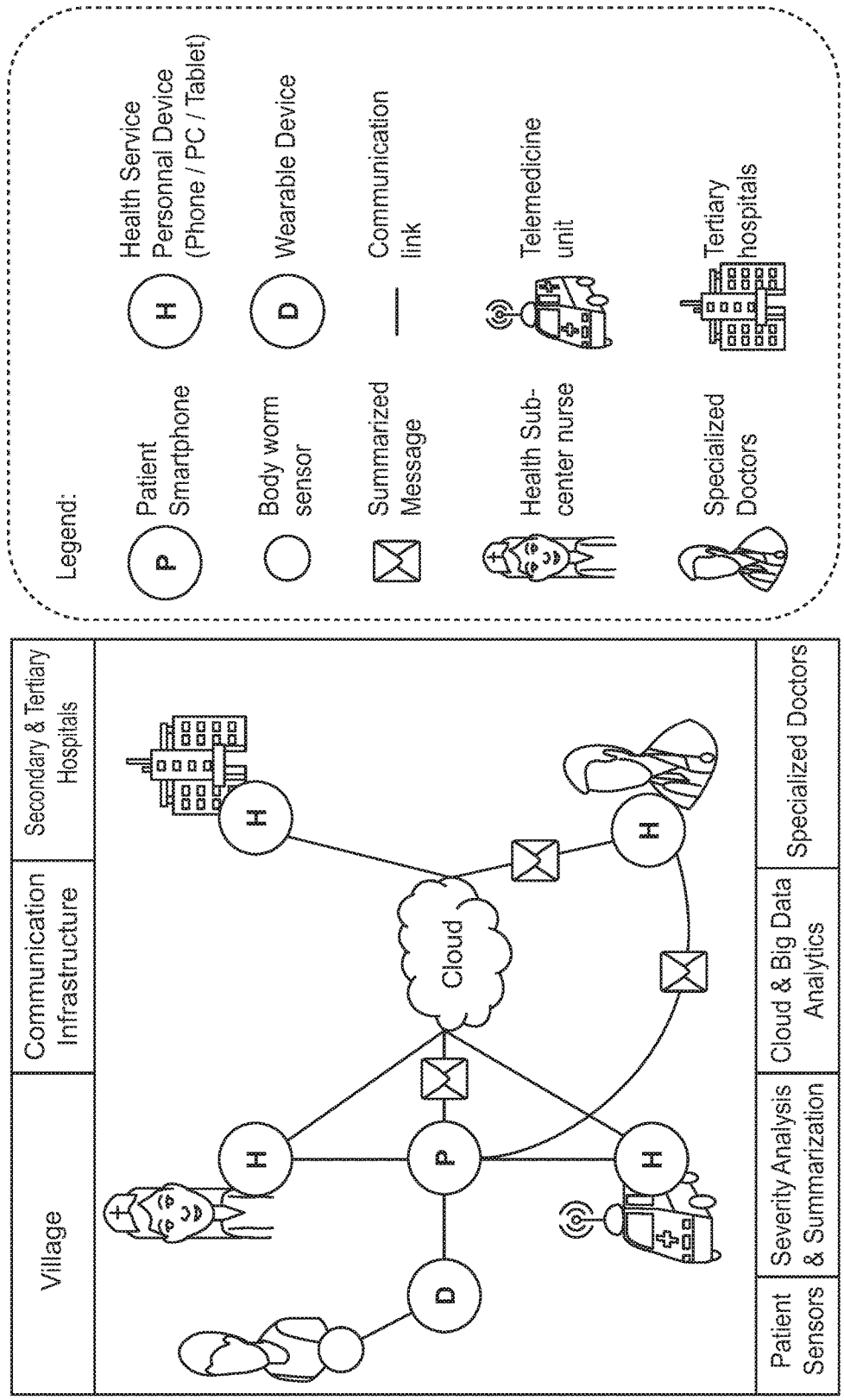
FIG. 7 illustrates a system for remote monitoring of vital parameters in patients.

A single sensor (ECG sensor) was used an example, as illustrated in FIG. 7. The system supports multiple sensors in a similar manner. A low power wearable device with 2 to 4 electrodes was attached to the body of the patient. The power management includes a buck-boost voltage regulator, a battery charge controller, and a battery fuel gauge. The main controller is an MSP430 microcontroller with SPI, ADC, I2C, timers and GPIO. An optional temperature sensor provides the body temperature monitoring. An extremely power sensitive firmware controls this device and manages its connectivity to the mobile phone.

A number of patients are remotely monitored through the system by a number of doctors and/or nurses. Each patient is provided with a wearable, battery-powered, and wireless data aggregation and transmission unit, which is worn as a necklace or placed on the waist. The body sensors are connected to the data aggregation and transmission unit using wireless connectivity. The wearable data aggregation and transmission unit connects to a PAS unit through the patient's smart phone, which is connected to the internet through 2G, 3G, or Wi-Fi network. The smart phone does a preliminary analysis to warn the patient of abnormalities, if any, specifically when internet connection is unavailable. The analytical storage engine of PAS unit does the backend storage and the signal processing of the acquired live signals before performing the required analytical diagnostics algorithm over the stream data. The server intimates the doctor, patient and the hospital monitoring service about the potential abnormality in the sensor signal. The doctor/hospital monitoring station may choose to connect to the server for the live sensor stream on their smart phone, tablet, or on a browser based web client. The doctor could further trigger an alarm to the patient about the criticality of his condition and further course of action.

Example 4

Evaluation of the Effectiveness of the RASPRO System

We measured both the diagnostic ability as well as the preventive predictive power of the RASPRO technique of rapid summarization for effective prognosis in wireless remote health monitoring. We formulated three hypotheses, Personalization Hypothesis, Precision Hypothesis, and Prevention Hypothesis and evaluated the effectiveness of RASPRO in satisfying these. Dataset: The first step to evaluate these hypotheses was to identify datasets that are extensive, long term and critically significant. We used large time series dataset from MIMIC II database, which contains multiple body sensor values from over 20,000 ICU patients. This dataset consists of ECG, ABP (Arterial Blood Pressure), HR, Non-obtrusive BP (NBP), SpO2, Mean Arterial BP (MAP), and other vital signs. From this, we selected a curated set of patient and control group data that contained a long time series data followed by a critical event.

We selected patients with Acute Hypotensive Episodes (AHE), which is a potentially fatal condition, found quite common in ICUs as well as caused due to postural hypotension. An AHE event is analytically identified as when MAP measurements remain below 60 mmHg for more than 30 minutes. This is a potentially fatal event and requires immediate intervention. We also made sure that the dataset provides uninterrupted MAP, and HR signals with a minimum sampling rate of 1 per minute, over at least 3 hours for both the event-patients as well as the control group. We selected a group of 30 patients (called group H) who had AHE during some time during their stay in ICU, and another 20 patients (called group C) who did not have AHE during their ICU stay. This dataset was selected from the PhysioNet challenge 2009. The H dataset also had a time marker $t_0$, after which AHE occurred in that patient within a one-hour window. Since the data was obtained from publicly available sources, we did not require getting prior approval of IRB for this work.

Evaluating Precision Hypothesis: The H and C group time series data comprising of Mean Arterial Pressure (MAP), of length T minutes prior to $t_0$ is modeled as a T-long feature vector (called the original time series OTS). These vectors are used for training (using 70% data, with 5 fold cross validation) and testing (using 30% data) an SVM model for classifying them as AHE or not. In effect, we try to classify sensor data prior to AHE event as a predictor for ensuing AHE condition. Since C group data did not have a time marker $t_0$ we selected a random but continuous time series of length T from each of the C group patients. The offset time window length T is varied as 30, 60, 90, 120, 150, and 180 minutes as an expanding time window. In the next step, the raw feature vectors are quantized using severity quantizer to form a quantized time series (QTS). The quantization levels (denoted by L) are varied as 5, 10, 15, and 20. For instance, when L=10, the each of the OTS MAP values between 60 mmHg and 50 mmHg are quantized into the same severity symbol, say "A−", whereas for L=5, the symbol "A−" quantizes all OTS MAP values between 60 mmHg and 55 mmHg. In the third step, the QTS are summarized and motifs extracted to form RASPRO Motif Time Series (MTS), with varying observation time window sizes W: 5, 10 and 15 minutes. The W corresponds to the time window in which all the severity symbols in the QTS is converted to a single consensus symbol. The QTS and MTS are then given as input to train and test the SVM model (one for QTS and another for MTS) for predicting AHE. A comparison of OTS, QTS, and MTS is done using the statistical measure of binary classification, the F-score. An F-score (also called F1 score) is calculated as:

$$F_1\,\text{score} = \frac{2*\text{Precision}*\text{Recall}}{\text{Precision} + \text{Recall}} \quad (14)$$

Figure 8A:
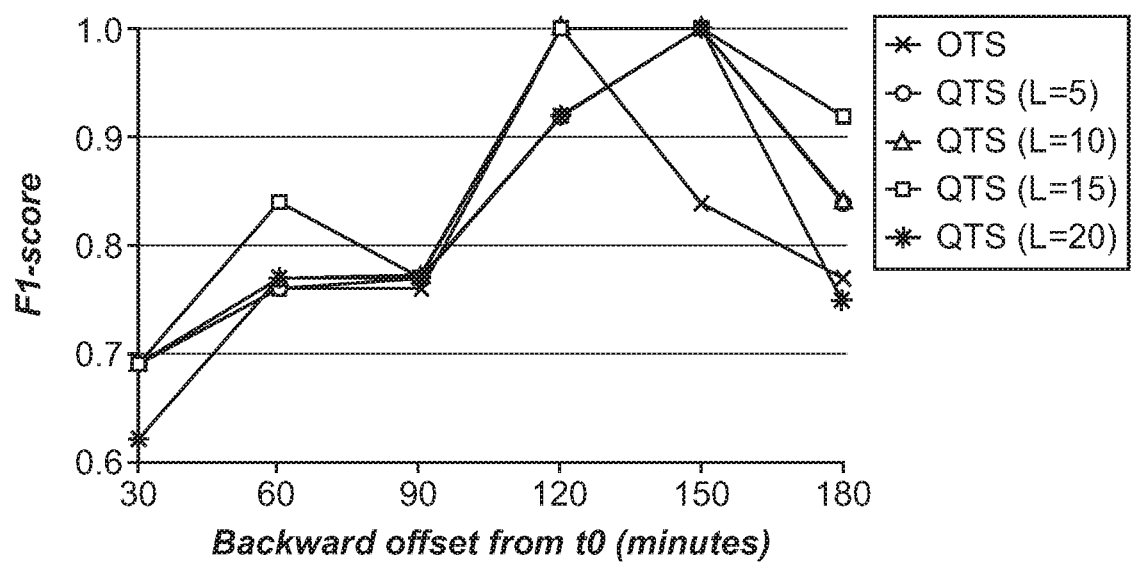
FIG. 8A shows the comparison of F1-score of OTS and QTS for classification of AHE using expanding time windows shows better performance of QTS with L=15.

From the comparative analysis of OTS and QTS as shown in FIG. 8A, we observe that QTS with L=15 has better F1-score in comparison to OTS in all the time-offsets T, although the root mean square error (RMSE) between these two series is an insignificant 0.001, pointing to the fact that OTS could be replaced with QTS. We select this QTS (L=15) and then compare it with MTS of varying time windows in FIG. 8B.

Figure 8B:
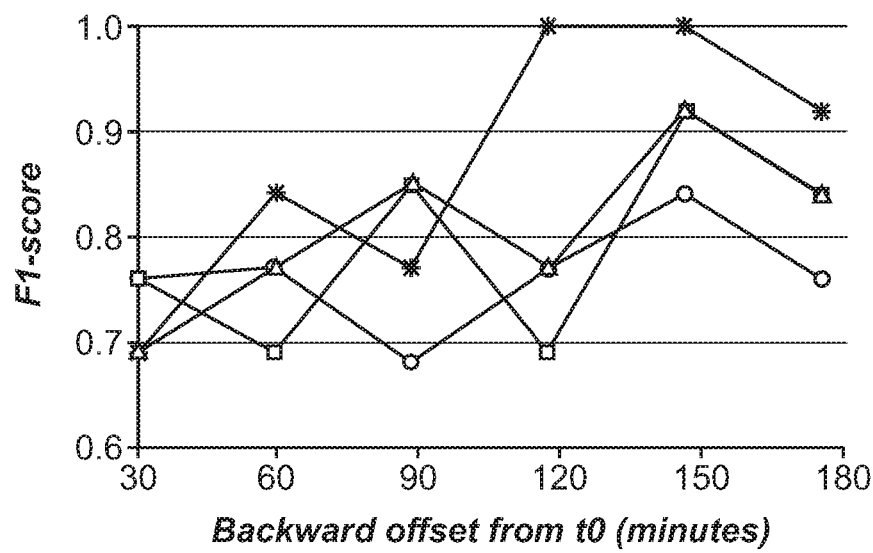
FIG. 8B shows the comparison of F1-score of QTS (L=15) and MTS (varying W) for classification of AHE using expanding time windows.
Figure 8C:
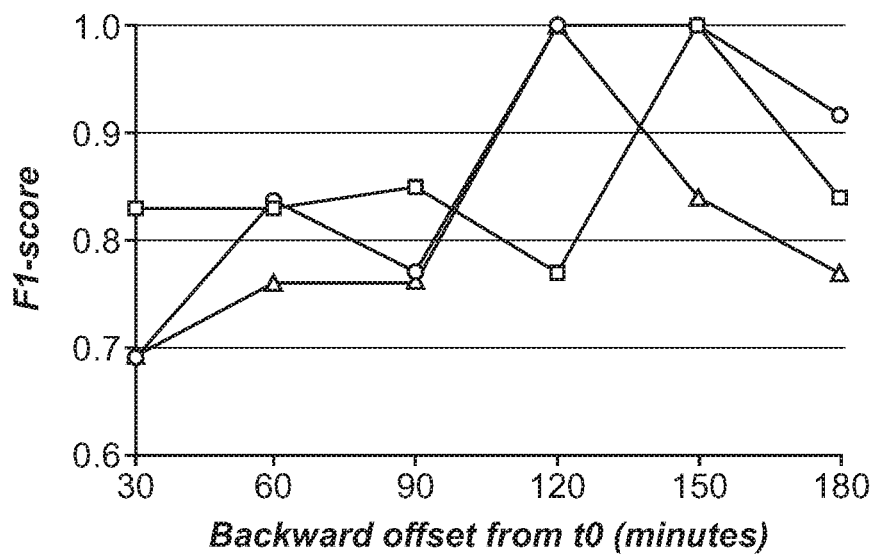
FIG. 8C shows the comparison of F1-score of OTS with QTSmax and MTSmax corresponding to best performing L and W values respectively for classifying AHE using expanding time windows.
Figure 8D:
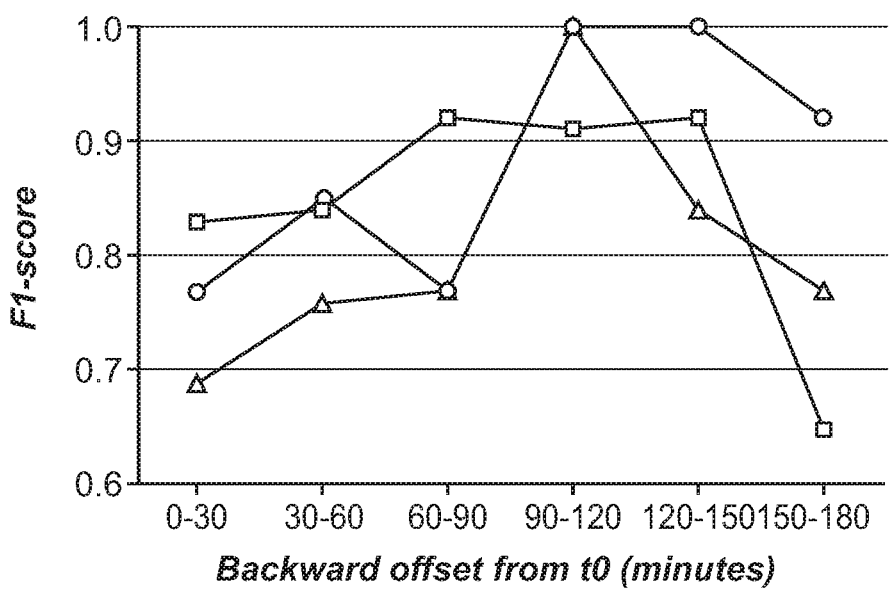
FIG. 8D shows the comparison of F1-score of OTS with QTSmax and MTSmax corresponding to best performing L and W values respectively for classifying AHE using moving window of 30 minutes duration.

We observe from FIG. 8B that QTS has higher F1-score compared to the best MTS with W=10. However, RMSE between QTS and MTS (W=10 and W=15) is a statistically insignificant value of 0.01, which implies that MTS using W=10 and 15 performs as good as QTS on an average across different time windows. Now, we further compare the OTS against the best performing L and W values corresponding to QTS and MTS respectively, and the results are plotted in FIG. 8C. These data points are marked as QTSmax and MTSmax respectively. In FIG. 8D, QTSmax and MTSmax show closely similar F1-score with the RMSE as 0.018. Going further, we used data from a moving window of 30 minutes each, instead of an expanding window. The comparative analysis of OTS against the best L and W values corresponding to QTS and MTS plotted in FIG. 8D show that MTS and QTS perform better than OTS in most of the time intervals, while the RMSE between MTS and QTS is 0.018 on an average. From these results, we can conclude that quantized symbols, as well as summarized motifs, are better in many cases and at least as good as raw time series in classifying the predictor data as AHE or not both in expanding and moving windows.

Evaluating Prediction Hypothesis: The next task is to find out if QTS and MTS can also be used as a priori data points for predicting future sensor values, which can further be used for generating critical alerts to warn the doctors ahead of time. For evaluating this, we use a data forecasting technique called ARIMA (autoregressive integrated moving average). This technique has been widely studied and used in time series prediction. In this technique we build a patient-specific ARIMA model by training it on 180 minutes of MAP data, and then use that model to predict the following 60 minutes of MAP values. The predicted and actual values are compared using the statistical measure of RMSE. First, we use OTS data for training and prediction. In the second experiment, the QTS data points are used for training, followed by the prediction of future raw time series data. These predicted raw time series values are compared with the corresponding actual OTS. Similarly, we repeat the same steps with MTS too.

Figure 9A:
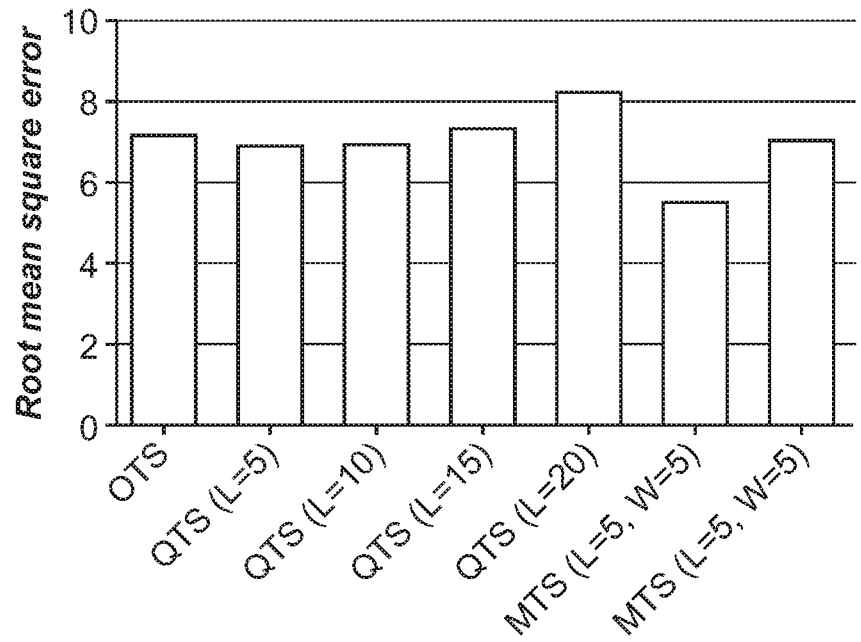
FIG. 9A shows the root mean square error for MAP prediction among group H patients using ARIMA model while using OTS, QTS (L=5, 10, 15, and 20) and MTS (L=5, and 10, while keeping W=5).
Figure 9B:
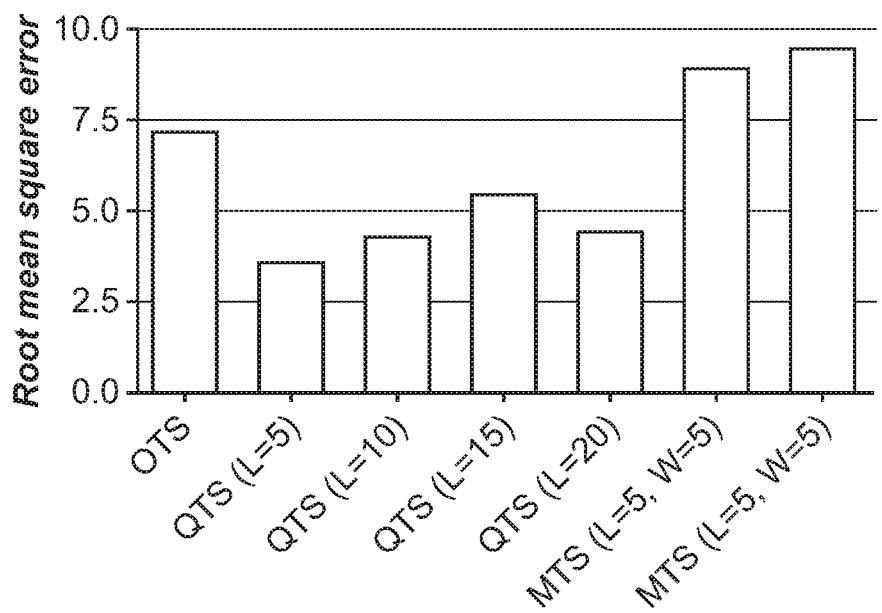
FIG. 9B illustrates the root mean square error for MAP prediction using ARIMA model for the control group patients while using OTS, QTS (L=5, 10, 15, and 20) and MTS (L=5, and 10, while keeping W=5).

FIG. 9A and FIG. 9B show the RMSE values while using OTS, QTS (with L=5, 10, 15, and 20) and MTS (with L=5, and 10, while using W=5) for H and C groups of patients. While using MTS, we had to restrict to using only a single window size of 5 since there were not enough consensus symbols for training the ARIMA model when the window size was increased to 10 and 15. FIG. 9A shows that among H group patients, the ARIMA models built using OTS, QTS, and MTS have very similar RMSE, while the least RMSE is observed when using MTS with L=5, and W=5. Among the C group patients as shown in FIG. 9A, the OTS and QTS show very similar RMSE, while MTS have at least 4 points higher RMSE in comparison. In this, the least RMSE is observed while using QTS with L=5. From these observations, we can conclude with certainty that RASPRO motifs and quantized severity symbols can be used for predicting future sensor values, even up to 60 minutes using a patient specific trained ARIMA model, thereby proving our prediction hypothesis.

Evaluating Personalization Hypothesis: The third hypothesis aims to find out if there are patient specific custom severity levels, and summarization frequencies, which if optimized could lead to better accuracies in diagnosis. For this, we further analyze our earlier results. We observe from FIG. 8C and FIG. 8D that by selecting different severity quantization levels (L) and through varying the summarization window size (W), we are able to predict the onset of AHE with higher F1-score. This supports an argument for using disease and time-specific L and W values for achieving better accuracy in classification problems. Furthermore, we see from ARIMA prediction results as shown in FIG. 9A and FIG. 9B that by using different L and W values among different groups of patients (or population) we can achieve better prediction accuracy. Hence, among high-risk patients, we can use MTS (L=5, W=5) configuration, while among other patients we can use QTS of (L=5 or 20) for best results. These results further support our third hypothesis, that there exists an opportunity for personalization at least at a sub-group or population level.

Though the above experiments using AHE are only representative of how step-wise precision, personalization, and prevention can be achieved using RASPRO, the practitioners as a whole agree that in wide-ranging scenarios patient-sensor-disease-time specific severity levels need to be defined that is both practical to manage alerts as well as effective in identifying emergencies.

IoT-Based Smart Edge for Global Health

The term Global Health denotes equitable access to healthcare, particularly in remote-rural-developing regions, and is characterized by unique challenges of affordability, accessibility, and availability for which one of the most promising technological interventions that is emerging is the Internet of Things (IoT), based on remote health monitoring. An IoT-based Smart Edge system for remote health monitoring is taught herein, in which wearable vital sensors transmit data into two novel software engines, namely Rapid Active Summarization for effective Prognosis (RASPRO) and Criticality Measure Index (CMI) alerts, both of which are implemented in the IoT Smart Edge. RASPRO transforms voluminous sensor data into clinically-meaningful summaries called Personalized Health Motifs (PHMs). A CMI alerts engine computes an aggregate criticality score. The IoT Smart Edge employs a risk-stratified protocol consisting of a rapid guaranteed push of alerts & PHMs directly to physicians, and best effort pull of detailed data-on-demand (D-on-D) through the cloud. Clinical validation and performance evaluation of the Smart Edge system has been accomplished. Clinical validation on 183 patients demonstrated that the IoT Smart Edge is highly effective in remote monitoring, advance warning, and detection of cardiac conditions, as quantified by three measures, precision (0.87), recall (0.83), and F1-score (0.85). Furthermore, performance evaluation showed significant reductions in bandwidth (98%) and energy (90%), thereby making it suitable for emerging narrow-band IoT networks. In the deployment of this system in a cardiology institute of a University hospital, it was observed that IoT Smart Edge helped to increase the availability of physicians by 59%. Hence, the IoT Smart Edge system is a significant step towards addressing requirements for global health.

Introduction

Global Health, by which is meant achieving equity in healthcare access for all people worldwide, is one of the huge challenges in many developing parts of the world, where close to three billion people reside in rural regions. In these regions there are many barriers in providing equitable medical care. There is a perceived lack of healthcare facilities both in terms of medical practitioners and diagnostic equipment. Many physicians are unwilling to serve in remote regions, as a result of which, most Government-established primary care centers are largely understaffed. For most patients in these regions, it takes a major part of the day to reach the nearest hospital facility, which makes it a big deterrent to undergo regular screening and checkups. For rural population who are primarily in low-income group and depend upon daily wages, taking a break to visit the hospital is an economic burden. Even when patients eventually reach a hospital, many a time, due to the high patient load and overcrowding, chances are that physicians are already too busy to give any consultation time.

One of the most promising technological interventions which is emerging to bridge this global health equity gap is the Internet of Things (IoT)-based remote health monitoring. IoT technologies enable sensing and continuous remote monitoring of physiological signals such as electrocardiogram (ECG), blood pressure (BP), blood oxygen (SpO2), blood glucose, as well as user activities such as sitting, standing, walking, etc. These monitored parameters can then be used for automated decision support systems that help physicians to arrive at early prognosis. This initiates a marked shift from the current practice of reactive disease-diagnosis-treatment methodology towards a proactive prognosis-health-management approach.

More recently, pilot deployments of specially tailored IoT networks, such as the one based on narrow-band technology (NB-IoT) in different parts of the world are being seen. These networks are designed for low-power IoT devices that send only a few bits of data at a time. Though these are early days in the deployment of such IoT networks, in the near future such disruptive technologies can have far-reaching impact both in terms of the quality of healthcare services offered to the patients and the overall cost of healthcare delivery. As a result, IoT based systems have generated a lot of interest among researchers.

To make IoT-based remote health monitoring systems suitable for global health deployment, particularly in sparsely-connected remote and rural regions, a significant step forward is made by introducing context-aware, healthcare domain-specific intelligence into IoT gateways. An IoT-based smart edge system is taught herein, which the inventors term Amrita IoT Medical (AIM) Smart-edge, developed for remote health monitoring. In order to address the challenges of delivering health care effectively in the global health scenario, AIM smart-edge has the following novel technical contributions:

Wearable IoT-based vitals monitoring devices (called as AIM-Vitals) which include a 3-lead ECG sensor and a photoplethysmograph (PPG) sensor. From the ECG sensor, parameters such as RR interval, QTc, QRS width etc., and from the PPG sensor, parameters such as blood pressure (BP), blood oxygen (SpO2) and pulse rate are obtained.

Rapid Active Summarization for effective prognosis (RASPRO): a software algorithm that converts voluminous multi-sensor patient data into clinically interpretable summaries in the form of severity symbols that we call Personalized Health Motifs (PHMs).

A timely alerting technique that translates the PHMs into an aggregate Criticality Measure Index (CMI), and a risk-stratified alerts and data delivery protocol that uses adaptive bandwidth aware techniques such as: (a) PHM-on-Alert that pushes alerts directly from AIM Smart-edge to physicians and (b) Detailed Data-on-Demand (DD-on-D) using which physicians pull detailed data through the cloud.

Development of such IoT based remote health monitoring systems must be carried out as an inter-disciplinary effort, in which physicians are intimately involved in how the data is captured, summarized, analyzed, transmitted, and presented, so as to detect abnormalities and generate advance warning alerts accurately, promptly, and without omission. A prototype IoT remote health monitoring system consisting of the AIM Smart-edge, interfacing to a cloud running hospital information system, and the applications at the physician's end has been implemented. This has been deployed in remote regions in the southern state of Kerala in India. Clinical validation of this system in two steps: (a) field testing of AIM-Vitals on close to 100 patients and (b) Physionet dataset-based testing of RASPRO and CMI techniques on 83 patients for detecting and advance warning of cardiac diseases and acute hypotensive episodes.

Overall System Architecture

The IoT remote health monitoring architecture consists of three functional parts (see FIG. 10): AIM Smart-edge at the patient's end, an intermediary cloud, and visualization applications at the physician's end. First a high-level overview of these three parts and the networks connecting them.

A. Amrita IoT-Based Medical (AIM) Smart-Edge (1000)

The AIM Smart-edge consists of two IoT based components: the AIM vitals monitoring devices (AIM-Vitals) 1001 and the AIM-Gateway 1002.

1) AIM-Vitals: The AIM-Vitals 1001 are IoT based devices comprising ECG and PPG sensors that monitor parameters such as ECG, BP, pulse rate, blood oxygen saturation (SpO2), etc. The architecture provides flexibility to configure one of the sensors (such as ECG) as the master and others as slaves. These sensors transmit vital parameters to the AIM Gateway 1002 over different short-range wireless networks such as ZigBee, Bluetooth (BT) and WiFi, in that order of preference, whichever is available. Section IV describes in detail the AIM Vitals that have been developed.

2) AIM-Gateway: The AIM-Gateway 1002 can run on any of the following types of devices: (a) shared gateway devices 1003 installed to serve multiple patients in the same household or adjacent households, (b) patient's smartphone 1005 turned into a personal AIM-Gateway, or (c) the master AIM-Vitals device 1001 itself occasionally taking on the role of a gateway for the slave nodes.

Option (a) is preferred for shared configuration in places with reliable power source. Option (b) provides connectivity while the patient is ambulatory, whereas option (c) minimizes the cost though it puts limits on the computational power. The AIM-Gateway runs two AIM Smart-edge applications. First is the RASPRO Summarization Engine 1004 that generates the Personalized Health Motifs (PHMs) and second is the Alerts Engine that evaluates the Criticality Measure Index (CMI)1006 and transmits timely alerts. Sections V and VI elaborate these two applications respectively.

The AIM-Gateway also connects to the cloud 1007 through data networks where available, and directly to physician 1008 over mobile/cellular networks or emerging IoT networks. These emerging IoT networks are generally based on Narrow-Band technology (NB-IoT in short) and typically supports downlink/uplink bandwidths in the range of 30 KBps.

In order to accommodate all of the above types of heterogeneous networks, the AIM Smart-edge employs high performance bandwidth-miserly message transmission protocol to communicate with the physicians both directly and through the cloud. This is elaborated in Section VII.

B. Cloud

The cloud 1007 broadly hosts the Amrita Hospital Information System (HIS) which is a publicly available CCHIT certified J2EE based health informatics suite. It serves as the archival database storage for all patient records with adequate access control, security, privacy, and reliability. HIS also supports running special purpose data analytics algorithms on anonymized patient data.

C. AIM-View

The third part of the architecture is called AIM-View (1008), which is an application that runs on android devices and web platforms belonging to physicians (who may be family practitioners, specialists and other healthcare providers). AIM-View helps the physicians to receive and visualize patient data. Based on this they can suggest interventions remotely to the patients or their caretakers. AIM-View also allows physicians to set and tune sensing frequency, transmission timing, summarization intervals, and other variables in the AIM Smart-edge.

D. General Results

The AIM Smart-edge has been clinically validated in two steps: (a) field testing of AIM-Vitals on close to 100 patients and (b) Physionet dataset-based testing of RASPRO and CMI techniques on 83 patients for detecting and advance warning of cardiac conditions. The results from other validation, elaborated in Section VIII, are very encouraging: AIM-Vitals performed as good as gold standard devices used in clinical practice. RASPRO PHMs demonstrated their diagnostic effectiveness, as measured by standard metrics of precision, recall, and F1-score (with values equal to 0:87, 0:83, and 0:85 respectively). From these results it is concluded that the PHMs have excellent clinical effectiveness, and this is attributable to the premise that PHMs effectively capture the major abnormal trends for a first level clinical diagnosis and suppress details that can be deferred for a subsequent detailed investigation.

We also evaluated the system performance of AIM Smart-edge for its suitability to global health deployment. Our evaluation, elaborated in Section IX, demonstrates the following advantages (also referred to as the three A's):

Accessibility: Both RASPRO and CMI techniques are implemented on the AIM Smart-edge itself, and PHMs/ Alerts transmission protocols are designed for emerging narrow-bandwidth IoT networks (NB-IoT). Our performance evaluation shows that RASPRO results in significant bandwidth savings (of at least 98%), accompanied by 90% average reduction in energy consumption as well.

Affordability: The AIM-Vitals that we have developed are frugal innovations in terms of cost. They are at least three times less costly than existing off-the shelf products but provide a richer set of clinically useful features. Additionally, the RASPRO and CMI techniques reduce the recurrent data bandwidth cost for sending medical sensor data to remote physicians.

Availability: The CMI based alerts give the dual advantages of: (a) ensuring that physicians can focus their time and attention on the neediest of the patients, and (b) reducing unnecessary hospital revisits for the patients who do not show any criticality. Our evaluation shows that CMI-based alerts effectively segregate the patients needing urgent intervention, while reducing the need for hospital revisits among normal and low criticality patients by up to 59%. The availability for new patients is, therefore, increased by the same percentage.

IoT-Based Medical—Vitals Monitoring Devices
(Aim-Vitals)

Figure 10:
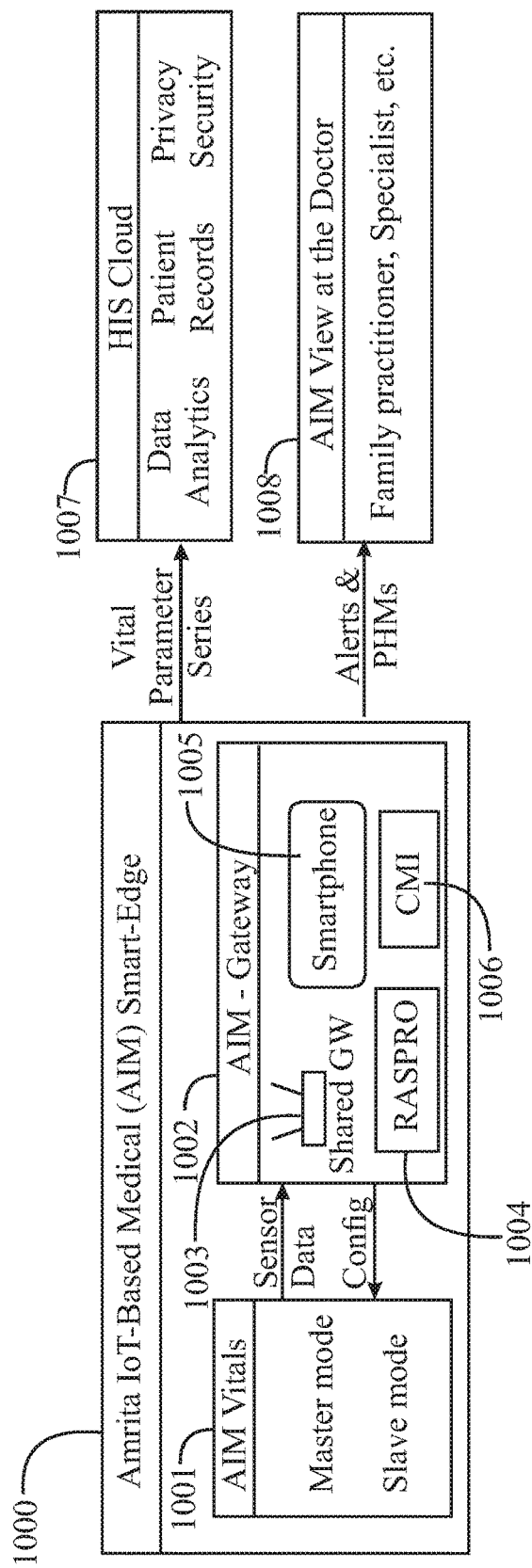
FIG. 10 is an architectural diagram of an Amrita IoT-based Medical remote monitoring system in an embodiment of the invention.

FIG. 10 is an architectural diagram of an Amrita IoT-based Medical remote monitoring system in an embodiment of the invention, showing vitals 1001, gateway 1002, modem 1003, smartphone (optional) 1005, CMI 1006, HIS cloud, and AIM view at a doctor's platform.

Figure 11:
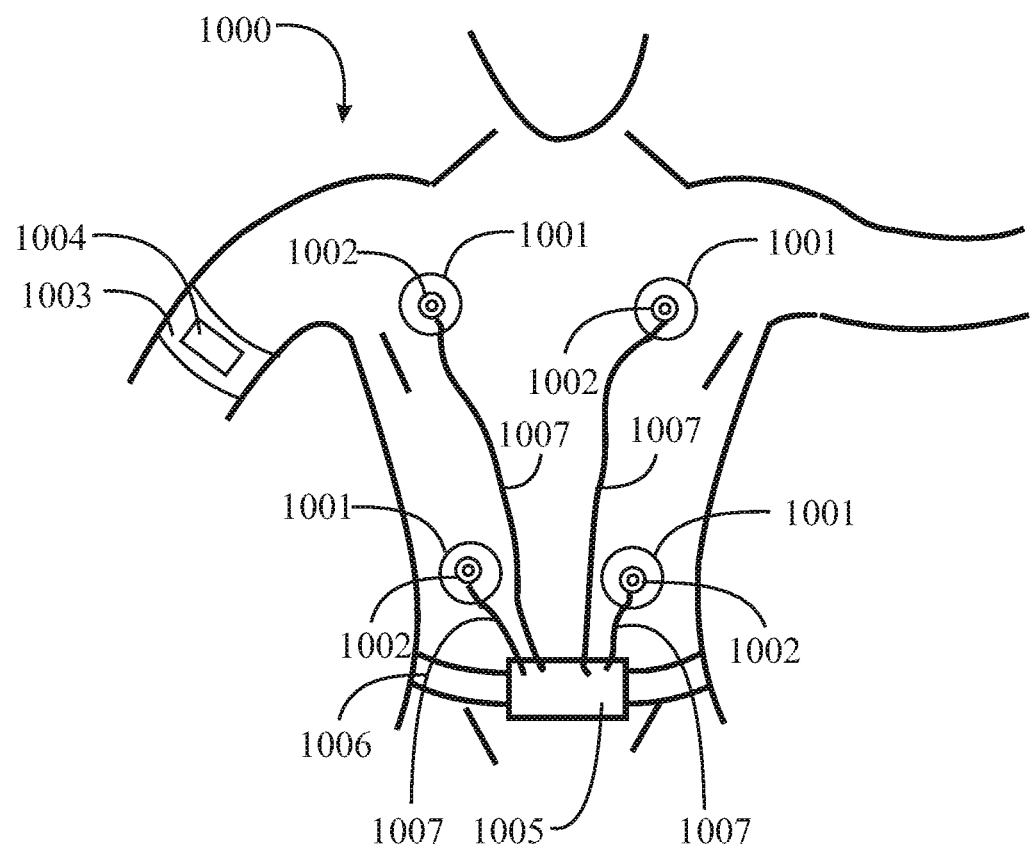
FIG. 11 illustrates IoT sensors applied to a patient's body in an embodiment of the invention.

FIG. 11 depicts a male torso with the AIM-Vitals wearable sensor nodes and related equipment. Four nodes 1002 are shown adhered with pads 1001 in four locations on the torso. These nodes may be of different sorts as described below. The nodes transmit sensed data to the AIM Gateway via one of ZigBee™, Bluetooth™ or WiFi network protocol, in that order of preference. Additionally, in FIG. 11 a wearable sensor 1004 is shown on an armband on the same body.

AIM-Vitals comprise the following wearable sensor nodes, shown in FIG. 11:

A. A 3-lead ECG sensor node, from which, multiple parameters such as QRS width, QTc, R-R interval, S-T elevation/depression, P-R interval, etc., are derived.

B. A photoplethysmograph (PPG) sensor node, from which multiple parameters such as blood pressure (BP), blood-oxygen (SpO2), and pulse rate, are derived.

AIM-Vitals' ECG sensor node has the following architectural components:

A. Sensor: The sensor chip is an ADS1292 ECG front-end from Texas Instruments, which is used for analog signal acquisitions. The ADS1292 outputs 24 Bit samples at sampling rates of up to 8 KHz. The chip interfaces to the microcontroller (MSP430) through an SPI interface.

B. Communication: A RN42 class-2 Bluetooth SPP (serial port profile) is used for establishing a low power wireless link from the AIM-Vitals to the AIM-Gateway. RN42supports low power sniff and sleep modes enabling longer battery life.

C. Power: A standard lithium-ion 3.7v, 890 mAH battery is used as the power source. The battery is charged using micro USB connector and one charge can support up to 24 hours of continuous ECG parameter monitoring and transmission.

D. Packaging: The board and the battery are enclosed in a 3D printed case. It provides the user with one power on/off button and one auxiliary button for custom/debug function. One of the two multi-light LEDs display the battery status, while the other shows the device status: connected, disconnected, searching for AIM-Gateway, receiving signal, and debug modes.

E. Leads: A standard set of four unshielded thin cables are modified and connected to the board through a 3.5 mm jack. Three of these cables are used to collect the differential voltage signals, while the fourth cable is used as the right leg drive for reducing noise in the collected signal. The four electrode cables are attached to a patient's body through wet/dry electrodes in two different configurations that outputs either: (a) Mason-Likar limb leads I and II, or (b) any two Modified Chest Leads (MCL) such as MCL-V1 and MCL-V5. The AIM-Vitals' second sensor is a PPG sensor node which uses the reflection data in Infra-Red (IR) and Near-IR frequencies, from which are obtained BP, SpO2, and pulse rate.

The ECG and PPG sensor nodes can be configured in two ways depending upon how the sensing interval consisting of start time, end time, and frequency are set.

A. Master-slave: AIM-Gateway assigns one of the nodes as the master, which in turn will ensure time synchrony between the respective parameters captured from the slave node.

B. Peer-to-peer: AIM-Gateway sets the sensing intervals directly and independently on each of the sensor nodes. The choice of the configuration depends on the targeted disease condition. For instance, in a hypertensive patient with a risk of stroke, the PPG device may be preferred as the master so that it can trigger the ECG device to start sensing whenever there is a medically significant upswing (>10 mmHg in less than 2 minutes) in the BP value. Alternatively, in an asymptomatic cardiac patient, the various vital parameters may be monitored in a peer-to-peer configuration, each at its own medically determined minimum frequency.

The raw sensor data coming in from the AIM-Vitals could be as large as 95 Mb/hour (with the ECG sensor contributing 80 Mb/hour and the PPG sensor contributing 15.8 Mb/hour). On the other hand, the IoT networks are expected to be of low bandwidths to support a large number of IoT nodes, with reduced energy usage. Hence, we need to summarize the data. However, any summarization technique poses a danger of losing clinical utility and interpretability of data for the physicians. Our challenge was to develop a summarization technique based on medical expertise such that it largely preserves the clinical value for a first level of diagnosis. This novel technique which runs on the AIM Smart-edge is called RASPRO and is described in the next section.

Rapid Active Summarization for Effective Prognosis

Consider the raw sensor data coming in from AIM-Vitals' ECG and PPG sensor nodes. There are four major processing steps (see FIG. 12).

Step 1: From the sensor data, we derive, through parameterizer 1203, N different vital parameter series, V PS1, V PS2, . . . , V PSN. For example, in our case there would be five ECG (QRS width, QTc, R-R interval, S-T elevation/depression, P-R interval) and three PPG (BP, SpO2, pulse rate) parameter series, totaling up to N=8.

Step 2: Each sample value in each of the vital parameter series is converted by Severity Quantizers 1204, 1205 and 1206 to disease-parameter specific discrete quantized severity level symbol such as, 'A', 'A+', 'A++', 'A−', 'A−−', etc., where the clinically defined normal range for a given parameter is assigned the symbol 'A', while values which are above and below normal ranges are assigned with increasing number of "+" and "−" suffixes according to the severity. Unlike typical systems with fixed severity thresholds for a sensor, in RASPRO the number of severity level symbols LSV R and their mapping to corresponding parameter value ranges are customized according to the patient's disease as perceived by the physician.

Disease and Parameter Specific Severity Representation:

Vital parameters have generally predefined medically accepted severity ranges. However, in personalized monitoring, these ranges need to be tailored to target the specific disease condition of the patient. Moreover, specialists could assign non-identical thresholds for the same parameter, based on the organ of concern. For example, whereas a physician looking for cardiovascular complications in a patient would set the BP severity threshold at ≥130/85 mmHg, an ophthalmologist would set the same threshold at ≥160/95 mmHg, while looking for hypertensive retinopathy. This essentially makes the severity ranges disease and parameter specific.

Illustrative Case:

From an ECG signal, multiple parameters such as RR intervals, QTc, QRS width etc. may be derived. Each of these parameters would be quantized according to different normal/abnormal levels depending upon the disease condition of the patient. As an example in patients with heart disease, depression/elevation of the ST segment by 1 mm, 2 mm or 3 mm is indicative of ischaemia to the heart in increasing severity, and would be quantized as A+, A++ and A+++ respectively. Similarly, an RR interval less than 600 ms (A−) is indicative of a simple tachycardia, whereas, between 428 down to 250 ms (A−−) points more towards supraventricular arrythmias. In even critical arrhythmias such as ventricular tachycardias, the QT intervals are of concern, where QTc can be quantized as normal between 360-425 ms (A), borderline between 450-500 ms (A+), and abnormal as less than 500 ms (A++).

Output of step two are multiple series of quantized severity level symbols corresponding to different parameters.

Step 3: In this step, the quantized severity symbol series of all parameters relevant to the disease condition being monitored are grouped into a two dimensional Disease Severity Matrix (DSM) by multiplexer 1207 in the AIM Smart-edge. Each row R in the DSM represents one parameter, and the number of columns C represents the total number of samples in the monitoring interval. In addition to the names of the parameters, the following variables are set by the physician for DSMs based on the patient's disease condition:

T: start time of the monitoring interval
W: duration of the monitoring interval
F: sampling frequency The above factors are set to a synchronized value for all parameters grouped within the DSM. There may be a succession of DSMs 1208 for successive monitoring intervals with a quiescent time gap of δ between them.

Illustrative case: Suppose the physician wants to monitor three parameters such as BP, SpO2 and pulse rate one hour per day for a patient. Assuming severity symbol sampling frequency F=5/hr for all parameters, the DSM will have C=5 columns representing the number of samples per monitoring interval, and number of rows R=3. One such DSM is generated per day.

Figure 12:
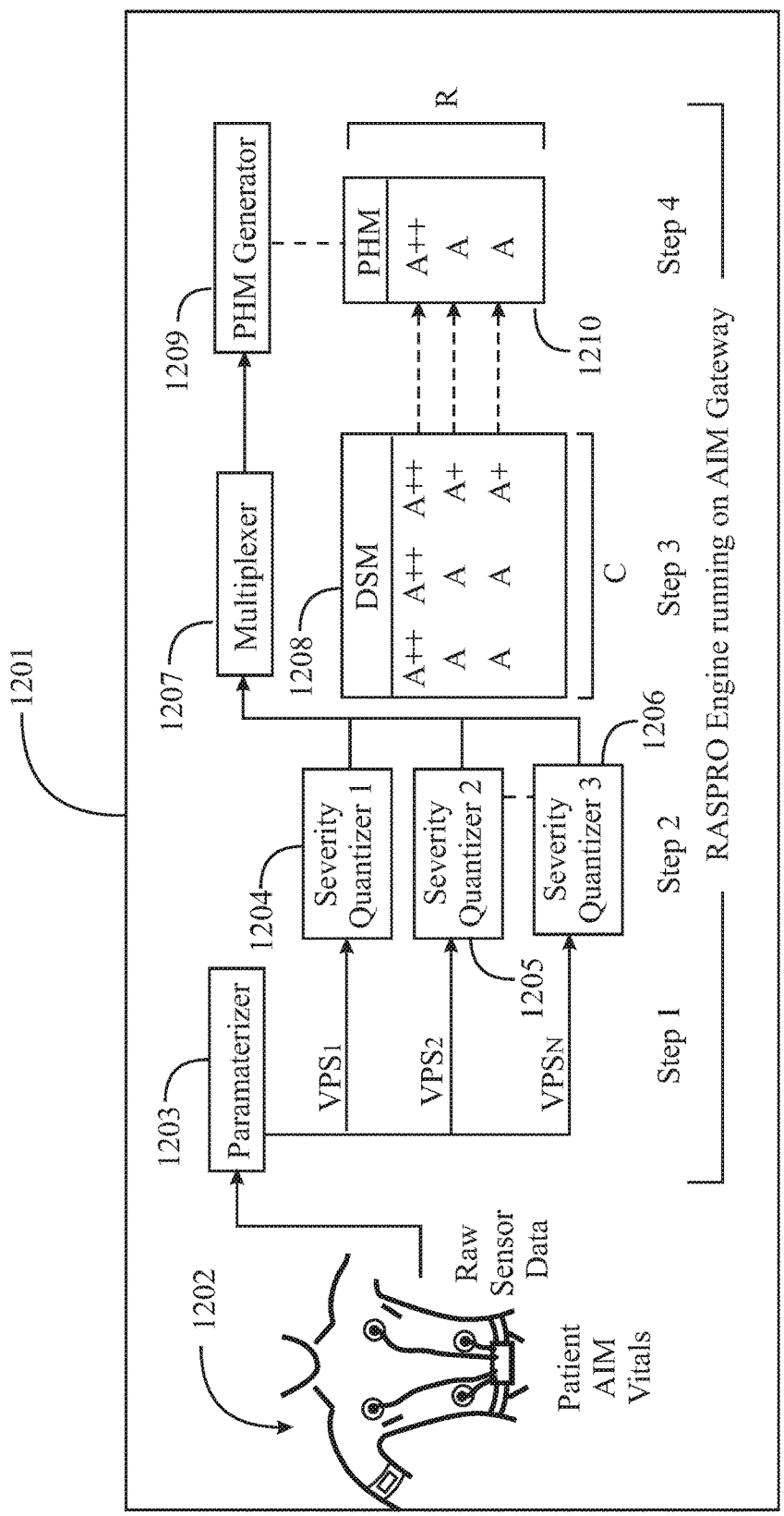
FIG. 12 illustrates four steps in sensing and processing sensor readings in an embodiment of the invention.

Step 4: In the final step of RASPRO, all the quantized severity symbols in a parametric row of DSM are temporally summarized to one consensus symbol using a disease parameter specific formulation. In general, the consensus symbol captures the dominant trend in the patient data. FIG. 12 depicts one such example where there are three rows in the DSM corresponding to three parameters, namely BP, SpO2, and pulse rate. Each of these parametric rows is summarized to consensus symbols (which are defined here as the most frequently occurring symbol) "A++", "A", and "A", respectively.

Personalized Health Motifs—Clinically Relevant Summarization:

Consensus symbols corresponding to all the rows in a DSM are put together in a column vector by PHM generator 1209 to arrive at a Personalized Health Motif (PHM) as depicted in FIG. 12. Different kinds of summarization based on the sensor type, diagnostic interest, and patients' health condition are possible. Depending up on these factors, the physician might want to know the mean of values, frequency of peaks, value of highest peak, most frequent abnormality, sparsity of values, etc. Accordingly, the RASPRO provides a framework to define summarization differently for various clinical requirements.

Illustrative Case:

For detection of acute hypotensive episodes from BP values, we derive the PHM corresponding to a DSM (of R parameters and C columns) as follows.

Let the multiset Θr denote all the severity symbols of r-th parameter (i.e., row) of the DSM.

$$\Theta r = \{\alpha r, 1, \alpha r, 2, \ldots, \alpha r, c, \ldots, \alpha r, C\}. \quad (1).$$

Note that a multiset allows multiple occurrences of same elements. Let σ r,c denote the sum of hamming distances of the severity symbol αr,c from every other severity symbol in Θr (taken pair-wise). σ r,c=Σ C i=1hamm dist(αr,c, αr,i) where each severity symbol α is regarded as a string of characters 'A', '+', and '−'. Define a multiset Ψr of all such r,c: Ψr={σr,1, σr,2, . . . , σr, c, . . . , σr, C}.

Now, define consensus symbol of the r-th parameter as:

Consensus Symbol, αr,CON is a severity symbol among all the symbols in Θr such that, its sum of hamming distances from all other symbols, which is represented as σr,CON, is the minimum value in Ψr, and is formulated as:

$$\alpha r, CON = \{\alpha r, i : \sigma r, i \text{ is the minimum in } \Psi r\}. \quad (2)$$

In case there are more than one αr,i for which the σr,i satisfies the above minimum criterion, then the highest severity symbol among those αr,i is selected as the αr,CON.

Define the Personalized Health Motif (PHM) as a vector of consensus symbols computed for the R parameters in the DSM of a patient P, and is represented as <α1,CON, α2,CON, . . . , αR,CON>.

If we were to compare and contrast RASPRO with traditional data compression and fusion techniques, such as those based on Fourier, DCT, wavelet, etc., as well as, newer ones, such as online dictionaries referred to in Section II, these techniques are mostly domain-agnostic (in the sense that they do not consider the clinical meaning of sensed parameter values while encoding). As a result, the compressed patient data does not lend itself to segregation based on severities set by medical experts, potentially resulting in loss of clinical interpretability, thereby missing clinically relevant insights. It is shown in an earlier works that domain-agnostic summarization techniques such as Symbolic Aggregate approXimation (SAX), when employed on medical data could result in clinical inconsistencies; e.g., parts of normal and abnormal values being binned into the same quantization level.

Some of the traditional compression techniques may also require the signals to be periodic/quasi-periodic in nature, which may not always be the case. More often than not, their computational complexities are generally a bit on the higher side compared to what IoT Smart edges can handle. Nevertheless, after performing medically guided severity extraction and any consequent alert generation at the IoT gateway (using RASPRO), the raw sensor data could be re-routed through these traditional compression techniques prior to transmission to cloud, thereby suitably complementing RASPRO.

Machine learning techniques viz. classifiers are generally used to take in-patient data and output a diagnostic decision. Classifiers that are domain agnostic can result in misclassification unless trained on large and reliable enough datasets. Such datasets need to adequately represent the complete spectrum of variations observed for disease conditions. Currently, the number of diseases for which such datasets are publicly available is limited. Also, classifiers could be comparatively computationally complex to execute on an IoT Smart-edge, and hence are best suited to run on the cloud to aid in automated diagnosis.

From the above discussion, it should be clear that the roles played by RASPRO, traditional data compression, and classification methods can be highly complementary. While RASPRO generates computationally simpler but clinically interpretable PHMs and alerts for prompt and direct transmission from the IoT smart-edge (at the patient end) to the physician, compression reduces data sizes for transmission from the IoT gateway to the cloud, and classification techniques bring in the power of machine learning to aid in diagnosis utilizing large amounts of data at the cloud.

Next, take RASPRO a step further, from just deriving PHMs, to generating meaningful criticality measures that can promptly alert the physicians with advance warnings about their patients who need urgent attention.

Criticality Measure Index

In order to obtain a single value representation of a patient's criticality from the PHMs, we compute an aggregate alert score called Criticality Measure Index (CMI). It may be noted that for each patient, the same severity symbol, α (such as A, A+, A++ etc.), could be communicative of varying degrees of risk. For instance, A++ in BP level for a normotensive patient communicates higher severity compared to that in a hypertensive patient with history of prolonged high BP. We capture these dependencies in CMI computation, given a DSM and its PHM, using the following terms:

PHM(r): r-th element of the PHM vector, which is same as αr,CON

λP (αr,CON): a numerical risk indicator corresponding to the consensus symbol αr,CON, assigned specifically for a patient P by the physician. Since αr,CON is already a result of quantization that is disease and vital parameter specific, λP (αr,CON) becomes a disease-parameterpatient specific quantity.

γ(αr,CON): an optional multiplicative factor such as the frequency of occurrence of consensus symbol αr,CON in the corresponding r-th parametric row in DSM. In place of the frequency of occurrence, any other disease specific factors as suggested by the physician can also be used. Using these, we now define CMI as follows:

$$CMI(P) = RX\ r=1\ [\lambda P(PHM(r)) * \gamma(PHM(r))].$$

Patient Specific Alert Generation: The λP (α) value is set by the physician considering the context of patient's health condition including historical medical records and specific vulnerabilities documented therein. For instance, λP (α) values will be increased in proportion to number of previous episodes of arrhythmias, ischemic strokes, or myocardial infarctions that a patient has undergone. Hence, it is a measure to distinguish patients based on their previous history even if they may have the same disease condition. The higher the perceived risk of the patient, higher would be the λP (α) value.

The CMI values are mapped to four qualitative alert levels: Critical, high, low, and normal, which are set by physicians based on maximum bounds of time of intervention that they feel permissible. The following are the broad clinical management approaches for these alert levels.

Critical alert level indicates immediate need for the patient to be taken to hospital.

High indicates opportunity for a short term remote intervention, but still the patient needs to see the physician on a high priority basis.

Low means that the patient's condition could be remotely managed.

Normal indicates that the patient is healthy. Since all the parameters are within the safe limits, the patient's condition could be ignored for the time being.

Figure 13:
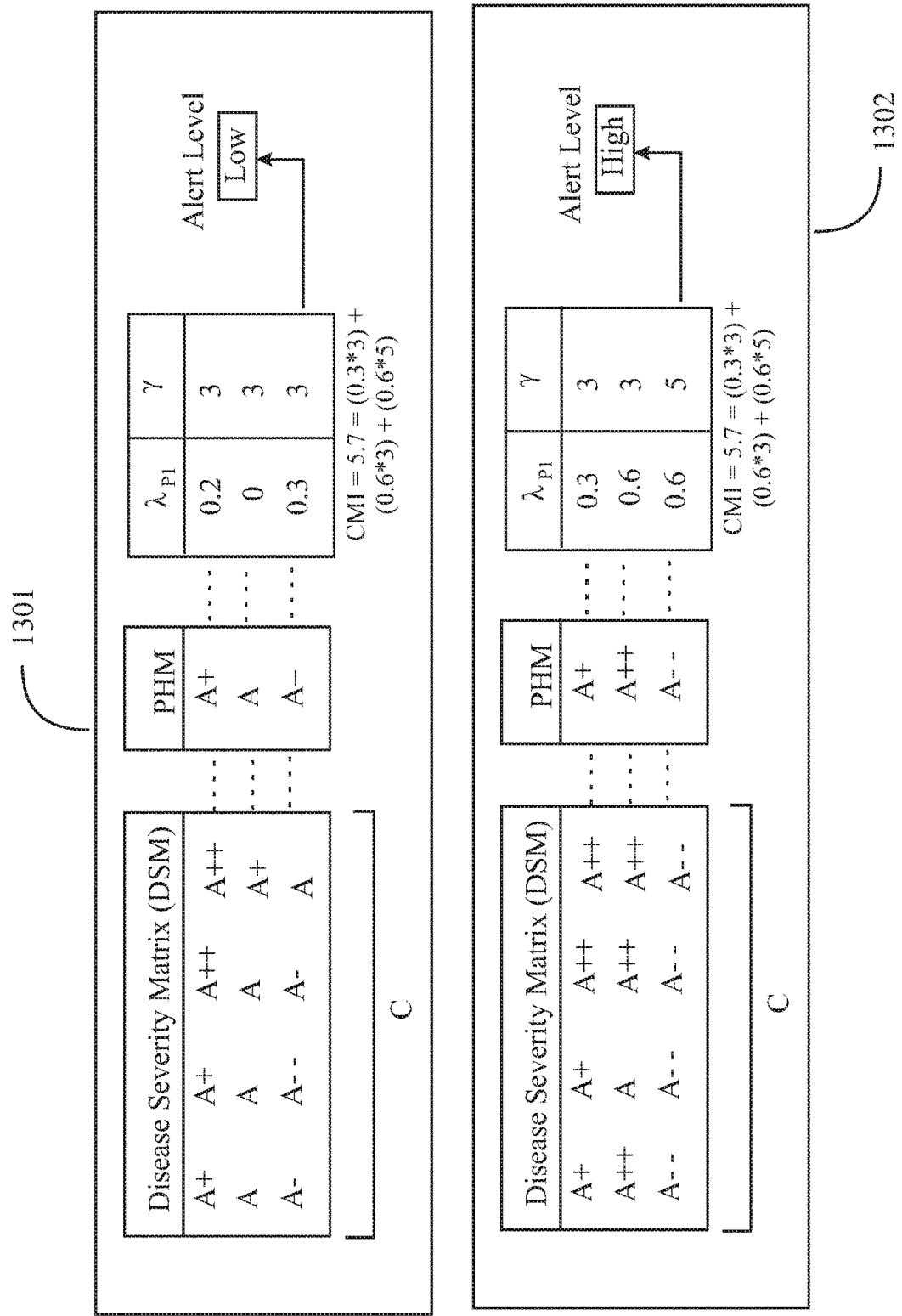
FIG. 13 illustrates determination of alert levels in an embodiment of the invention.

Mapping from CMIs to alert levels by the physicians also somewhat reflects the role of intuition in a largely subjective thinking process still widely observed in clinical practice among physicians in carrying out diagnosis. An example of CMI calculation and alert level mapping, with two patients is presented in FIG. 13. Here, considering the patient specific risk factors λP1, λP2, the CMI corresponding to level, whereas, P2's CMI of 5.7, which is greater than 2.7, is mapped to high alert level.

Apart from running the RASPRO and CMI alerts engines, the AIM Smart-edge also governs the advance-warning message push/pull protocol, which is described next.

Alerts and Data Delivery Protocol

Figure 14:
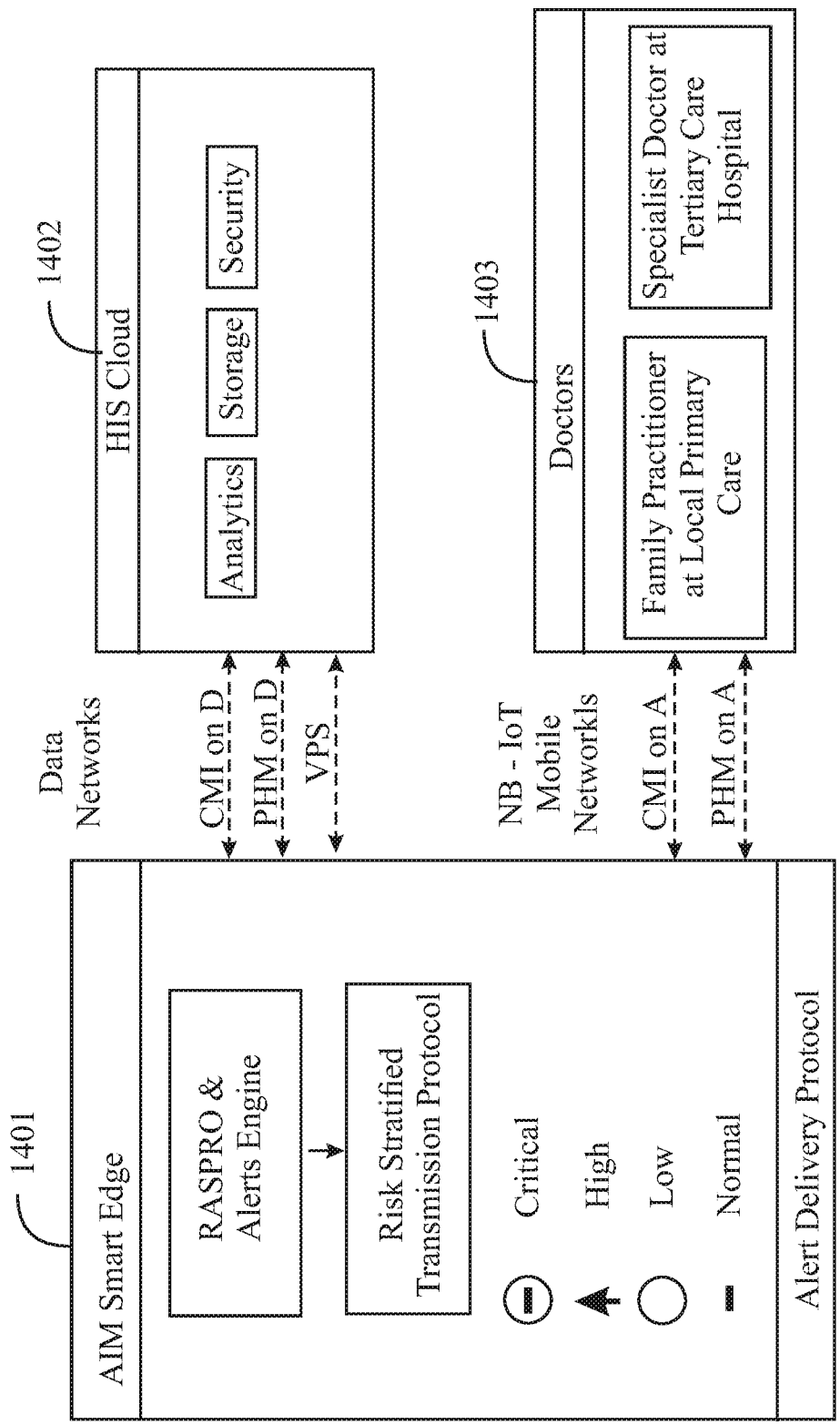
FIG. 14 illustrates an advance-warning message push/pull protocol in an embodiment of the invention.

In the remote monitoring system, we have developed and implemented an advance-warning message push/pull protocol (See FIG. 14) for transmission of alert levels and corresponding patient data from AIM Smart-edge 1401 to physicians 1403 both directly and via the cloud 1402. The protocol uses the following message primitives, as indicated in FIG. 14:

CMI-on-Alerts (CMI-on-A) are push messages of the patient's severity level (as one of four qualitative alert levels) and the corresponding CMI score.

PHM-on-Alerts (PHM-on-A) are push messages containing the PHM corresponding to current alert level.

CMI-on-Demand (CMI-on-D) is a pull request for CMIs. The response is CMI of the patient corresponding to the time interval requested.

PHM-on-Demand (PHM-on-D) is a pull request for PHMs. The response is PHMs of the patient corresponding to the time interval requested.

Detailed Data on Demand (DD-on-D) is a pull request for Vital Parameter Series (VPS), DSMs, and PHMs. The response may also include any analytics, based diagnosis/prognosis data corresponding to the time interval requested.

All the message primitives consist of a standard header containing the patient medical record number, timestamp and location of the patient. The CMI-on-A/CMI-on-D message is typically 21 Bytes in size, whereas the size of PHMs depends upon the number of parameters. The exact bandwidth requirements of these primitives are evaluated later in Section IX. Using the above primitives, the risk-stratified alert delivery protocol between AIM Smart-edge, cloud, and physicians, corresponding to the four alert levels is as follows (see Table I).

TABLE I

| Alert Level | Patient Condition | Message | Sender - Receiver | Network | QoS* |
|---|---|---|---|---|---|
| Critical | Life threatening | CMI-on-A | AIM-SE to Doc | Mobile(Voice&SMS), NB-IoT[#] | I&G Best effort |
| | | PHM-on-A | AIM-SE to Doc | Mobile (SMS), NB-IoT[#] | I&G, Best effort |
| | | DD-on-D | AIM-SE to Cloud to Doc | Internet data | Best effort |
| High | Major abnormality | CMI-on-A | AIM-SE to Doc | Mobile(SMS), NB-IoT[#] | I&G Best effort |
| | | PHM-on-D | AIM-SE to Cloud to Doc | Internet data | Best effort |
| | | DD-on-D | AIM-SE to Cloud to Doc | Internet data | Background[##] |
| Low | Minor abnormality | CMI-on-D | AIM-SE to Cloud to Doc | Internet data | Best effort |
| | | PHM-on-D | AIM-SE to Cloud to Doc | Internet data | Background[##] |
| | | DD-on-D | AIM-SE to Cloud to Doc | Internet data | Background[##] |
| Normal | No abnormality | PHM-on-D | AIM-SE to Cloud to Doc | Internet data | Background[##] |

*Quality of Service, AIM-SE = AIM Smart-edge, Doc = physician.
[#]where available, I&G = Immediate & guaranteed
[##]Chosen for least bandwidth and energy costs majority incidences of A+(or A−) in the DSM is computed as 1.8 for patient P1, as shown in diagram 1301, and 2.7 for patient P2, as shown ion diagram 1302, and these become their respective low to high alert thresholds. Hence, P1's CMI of 1.5, which is lesser than 1.8, is mapped to low alert Critical Alert level indicates that the patient is in life-threatening condition and needs immediate medical help with possible transport to the nearest emergency care. When a patient shows critical level, the AIM Smart-edge sends CMIon-A directly to physician over SMS and also initiates a voice emergency call over the mobile network. The PHMon-A message is sent to physicians over SMS and NB-IoT wherever available. The VPS data can be pulled by physician using DD-on-D which is served over data networks using best effort Quality of Service (QoS).

High Alert level indicates major abnormality in the patient and a possible worsening into critical level. Hence, the physician is immediately informed of the CMI-on-A over mobile/cellular SMS or NB-IoT wherever available. The physician, based on his/her preliminary diagnosis, can initiate PHM-on-D and DD-on-D, which are served using best effort QoS over the cloud. Low Alert level indicates minor abnormality in the patient and hence needs to be remotely monitored. PHM-on-D is transmitted to the cloud as part of periodic (e.g., daily) update, which will ripple over to the physician for any remote management/intervention. The PHMs and DD-on-D are served to the physician using data networks.

For Normal Alert level patients, we only store the PHMs in the cloud, that too it is scheduled for archival based on the bandwidth and power constraints of the data network. The raw sensor data is discarded from AIM Smart-edge unless there are instructions to the contrary from the physician. All the on-demand pull requests are first routed to the cloud, and in case of non-availability of the data in the cloud, it forwards the pull requests to the AIM Smart-edge where the AIM-Gateway will serve these requests.

Upon receiving the alerts and PHMs, there could be feedback effects such as physician increasing the frequency of CMI computation to keep a closer watch on the disease progression in the patient.

Implementation and Clinical Validation

We have implemented our AIM Smart-edge and carried out a medium scale clinical validation at our super-specialty hospital. The AIM Smart-edge's RASPRO and CMI alerts engines run on the following types of devices: (a) shared android box installed to serve multiple patients in the same household or adjacent households and (b) patients' smartphones running Android. These applications also provide visual user interfaces to the patient to view ECG, SpO2, BP, and pulse rate parameters live as they are received from the AIM-Vitals.

Figure 15:
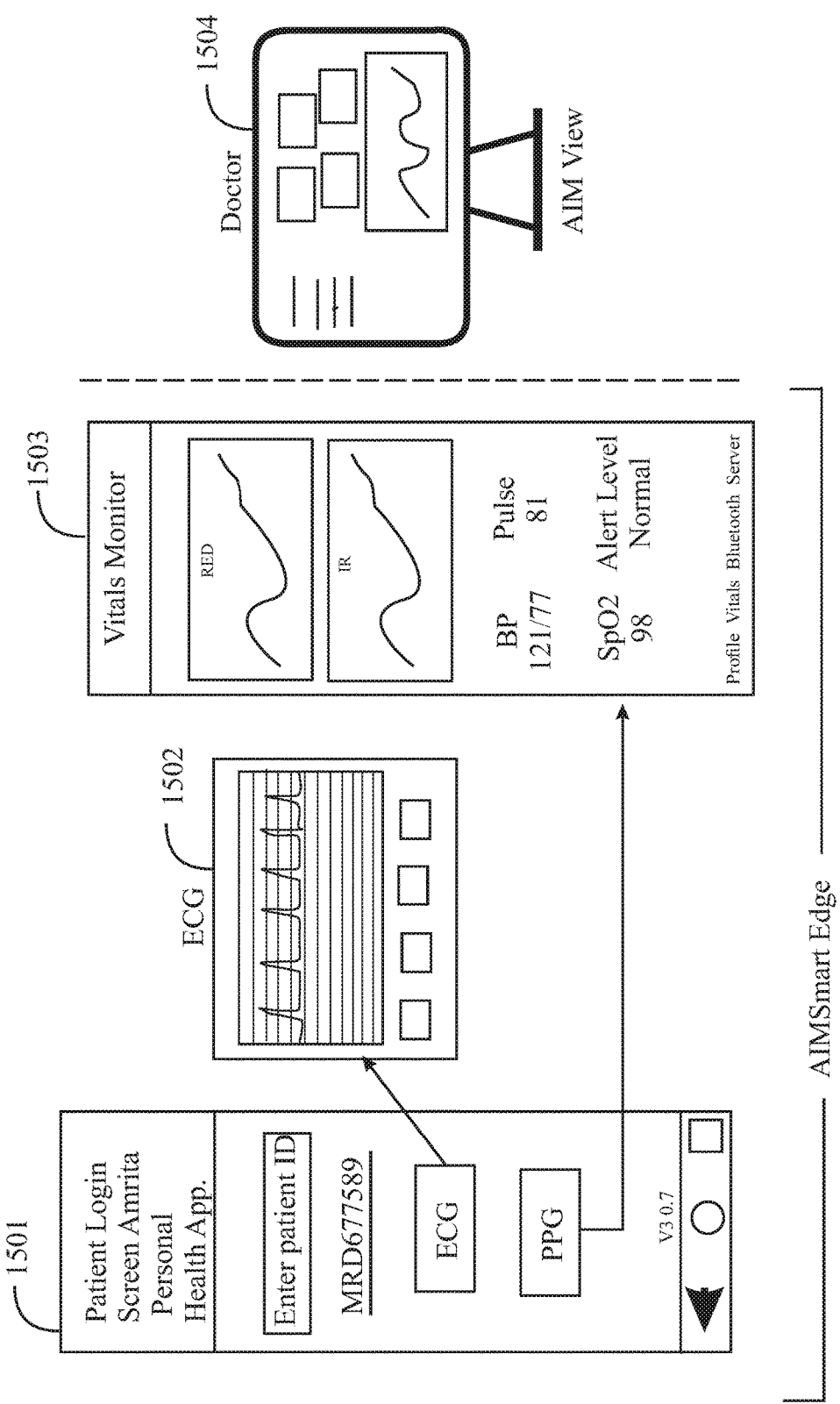
FIG. 15 shows various screenshots of the AIM Smart-edge application in an embodiment of the invention.

At the physician's end, we have implemented a web-based application that runs on both android smartphones and PCs to display the alerts, PHMs and sensor data. FIG. 15 shows various screenshots of AIM Smart-edge application, including a Login page 1501, an ECG display 1502, and a display of Vitals 1503, and an AIM-View web app at the physician's end. The intervening cloud server (not shown in the figure) was implemented using Tornado, while we used AngularJS for user interface scripts. The server was designed such that AIM Smart-edge could communicate to it using representational state transfer (REST) application programming interfaces (API) and exchange data using JavaScript Object Notation (JSON) format. It may be noted that the cloud also serves as a reliable data backup in the event of smartphone failure. Having implemented the prototype system as described above, we carried out a multiphase clinical deployment whose evaluation we elaborate below:

A. Clinical Validation: AIM-Vitals Sensor Nodes

University also runs a 1,500 bed super-specialty hospital to which 40 remote clinics are connected through Internet, by which physicians can carry out consultations with geographically remote patients, generally abbreviated in literature as Telemedicine. A total of 100 patients were selected from the hospital and the remote telemedicine network for our evaluation. Prior ethics committee approvals were obtained from the hospital as well as consent from the participating patients. The patient group had a variety of cardiac risk factors such as cholesterol, hypertension, etc. Many of them also had a history of myocardial infarction (MI), atrial fibrillation (AF), right/left bundle branch blocks, or had undergone cardiac surgery, valve replacements, and pacemakers etc. We conducted a three-phase validation:

Phase 1: In-Hospital Validation:

In first phase of validation, 25 patients in the hospital were selected to undergo the gold-standard Tread Mill Test (TMT). The average age of the group was 54 years. Each patient performed a sequential set of predefined exercises, such as walking at increasing speeds on normal and inclined tread mill surface. In all the patients, our AIM-Vitals ECG sensor node was attached along with the TMT machine and the data collected was stored in the AIM Smart-edge application. The measurements from AIM-Vitals ECG sensor node were clinically evaluated by two cardiologists in which they were asked to diagnose the patient condition based on their, age, profile, history, and the ECG data. This diagnosis was then compared with that obtained using standard TMT machine ECG data. The names of the patients were kept hidden to avoid any prejudice. Out of 25 patients, both physicians arrived at the same diagnosis in 24 patients and AIM-Vitals ECG data showed a satisfactory match with the standard TMT machine data. In one patient alone, AIM-Vitals ECG data showed some fine-grained differences because of its higher sampling rate of 500 Hz compared to 100 Hz of the standard TMT machine. This created minor ambiguity when the physicians analyzed the data, though it was subsequently resolved.

2) Phase 2: Ambulatory Setting:

In the second phase of validation, we obtained one hour of continuous ECG monitoring data from a set of 50 healthy individuals with an average age of 24 years, who wore the AIM-Vitals ECG sensor node while doing different activities such as: walking, climbing stairs, working in office, and exercising. Clinical standard TMT based ECG measurement duration, averages about 18-20 minutes per patient, which totals to 1000 minutes for 50 patients. In comparison, in our ambulatory validation we obtained 3000 minutes of AIM-Vitals ECG sensor data for the 50 patients so as to also capture variations associated with daily routine activities in those patients.

The data was recorded and analyzed for signal quality and usability for further analysis. The quality of data was found to be satisfactory for diagnostic purposes in 99% of time as assessed with signal to noise ratio as well as visual analysis. The only scope for noise in the data was traced to excessive sweating that displaced some of the ECG wet-electrodes.

3) Phase 3: Remote Deployment:

In the third phase of validation, we selected a telemedicine location in a remote rural setting about 300 KM from our hospital. This is a predominantly tribal region in the southern state of Kerala, India, with a stable electrical power connection. The patients from the tribal communities were provided with the AIM-Vitals, smartphones, and trained on how to use them. The AIM-Vitals ECG and PPG sensor nodes were used to collect and transmit data from a total of 53 patients. The data validation was later done by physicians using a blind review process. The results of the evaluation showed successful match between the AIM-Vitals sensor node data in all 53 patients and the corresponding reference data collected using standard hospital equipments. This remote deployment also brought up the training required for proper placement of ECG leads. In 10 other patients, there were situations where they placed the ECG leads in wrong configuration leading to invalid data collection. We learned that there is a need to train nurses in the use of IoT sensors, to properly place them on the patients to ensure valid data collection.

Next, we report the results from the clinical evaluation of our RASPRO and Alert Engines.B. Clinical Evaluation: RASPRO Engine. The RASPRO engine runs on the AIM Smart-edge and its outputs are the PHMs. The PHMs are highly summarized representations of the original raw sensor data. Hence, the question that we attempt to answer is whether the PHMs are clinically as good as the raw sensor data. We demonstrate with the help of three metrics, namely precision, recall and F1-score, that the PHMs are in fact as effective as raw sensor data for the purpose of clinical diagnosis in two representative disease conditions: (a) Atrial Fibrillation (AF) diagnosis which uses ECG PHMs and (b) Acute Hypotensive Episodes (AHE) diagnosis and prognosis which uses BP PHMs.

Atrial Fibrillation (AF) Diagnosis using ECG PHMs:

Atrial fibrillation (AF) is an irregular and often rapid heart rate that can increase a person's risk of stroke, heart failure and other heart-related complications. Physicians commonly use ECG to diagnose AF. Here, we set out to apply RASPRO on ECG and use the resulting ECG PHMs (in place of raw sensor data) to diagnose AF. The results of this clinical evaluation are as follows. We used more than 7,200 minutes of ECG data belonging to 10 patients from Physionet mIT-BIH Atrial Fibrillation (MIT-BIH) database. The data is partitioned into durations of AF and non-AF episodes and are annotated accordingly. In step 1 of RASPRO, we obtained two parameters from the raw ECG data: the RR intervals, and the corresponding difference between successive RR intervals, denoted as dRR (for delta RR). Next, in step 2 of RASPRO, we quantized the RR and dRR values using a uniform quantization step width of 25 ms.

In step 3 of RASPRO, we constructed a DSM with the number of rows R=2 (for RR and dRR parameters), and the number of columns C=32 (one DSM for every 32 cardiac cycles). Multiple such DSMs were constructed to span the entire duration of the ECG data.

In step 4 of RASPRO, we computed the consensus symbols and the corresponding PHMs. As guided by the cardiologist, in addition to the above set parameters, the consensus symbol is defined as the number of unique values appearing in a parametric row of the DSM, and is defined as follows:

$$\alpha r, CON = |Set(\Theta r)| \quad (4)$$

where, $Set(\Theta r)$ converts the multi-set $\Theta r$ (defined in equation 1) to a set which does not have any duplicate elements, and the cardinality of the set is assigned to $\alpha r, CON$.

The above equation captures the variability of the data, as it relates to the irregularity characteristic of ECG in AF patients. The PHM vectors were averaged, separately for AF and non-AF episodic durations over all the DSMs. The resulting PHM vector for AF episodes was found to be:

$$PHM\sim AF = (16.95, 15.10)$$

$$\text{with standard deviation } (2.53, 0.04) \quad (5)$$

where, the first term in the vector represents the $\alpha RR, CON$ and the second term represents the $\alpha dRR, CON$ values.

Similarly, in case of non-AF episodes, the average PHM vector was computed to be:

$$PHM\sim non-AF = (7.5, 5.6) \text{ with standard deviation}$$
$$(2.65, 0.005). \quad (6)$$

Therefore, by setting severity thresholds for $\alpha RR, CON$ and $\alpha dRR, CON$ as 12 and 9.5 respectively, we can segregate AF and non-AF episodes with precision, recall, and F1-score of 0.64, 0.97, and 0.77 respectively. These results validate the efficacy of RASPRO PHMs for clinical diagnosis of AF.

2) AHE Diagnosis and Prognosis using BP PHMs:

Acute Hypotensive Episode (AHE) is a condition resulting from a patient's Mean Arterial BP (which is directly derived from diastolic and systolic BP values) remaining below 60 mmHg for at least 90% of time during a time window of 30 minutes. This is a potentially fatal event and requires immediate intervention. We set out to use PHMs generated from mean arterial BP values for diagnosis and prognosis of this condition.

We selected AHE patient data from one of the most comprehensive sensor datasets, the MIMIC II. The dataset consists of mean arterial BP values of patient group (referred to as P) and control group (referred to as H). The data is sampled at one per minute. The P group contains 30 patients, and H contains 29. The P group had at least one AHE event during a 60 minute indow, while H group did not have any.

For diagnostic validation of PHMs, we selected from the P group, 60 minutes of mean arterial BP data that contained at least one AHE event.

For prognostic validation of PHMs, we selected from P group, 60-minute window of mean arterial BP data, prior to the onset of AHE. This time window is selected such that after this 60-minute window, the patient has had an AHE event within the next one hour. We also selected 60 minutes of mean arterial BP data from H group for comparative study purposes. The mean arterial BP raw sensor data is processed using the four steps of RASPRO. Step 1 is bypassed since the database already provides the mean arterial BP parameter.

In Step 2, the raw BP sensor data is converted to the corresponding severity symbols according to the following range of values:

For diagnosis: $40 < A\text{---} \leq 50$, $50 < A\text{--} \leq 55$, $55 < A \leq 60$, $A \geq 60$. Here, we assign any value above 60 mmHg the normal symbol 'A' since we are interested only in the AHE condition that is marked by a drop in mean arterial BP below 60 mmHg.

For prognosis: We observed that the data prior to onset of AHE did not generally show any significant and prolonged threshold crossing below 60 mmHg and was largely within the normal range. Hence, prognosis has to be drawn from disease specific fine-grained variations within the normal range but are indicative of AHE. So, assigning of severity symbols to mean arterial BP value ranges was done starting with a coarse width of 20 mmHg and then progressively using fine grained widths of 15 mmHg, 10 mmHg and 5 mmHg. The above ranges are set for AHE based on inputs from the physicians.

In Step 3, multiple DSMs are constructed with varying monitoring intervals starting with short 2 minutes up to longer duration of 30 minutes, such that these DSMs together span the entire 60 minutes. The dimensions of DSMs were accordingly determined as R=1 (since there is only one parameter), and C=2, 5, 10, 15, 20, 30.

In Step 4, diagnostic and prognostic PHMs are computed from these DSMs using consensus symbols, which are calculated using equation 2. In medical practice, AHE is one of the conditions that cannot be detected by simple visual observation of the severity levels of the vital parameters, and the most effective method known to detect AHE is through the use of machine learning, in particular, Support Vector Machines (SVM). We used SVM to evaluate the effectiveness of PHMs vis-a-vis raw BP data in arriving at an AHE diagnosis/prognosis. We created two trained SVM models, one using the raw data and the other using PHM. The SVM models were trained using 70% data and tested using the rest 30% data with fivefold cross-validation. In each of these models, the SVM was configured with two different kernels namely, rbf and linear, and we report the results from the best among them.

Diagnosis
    Raw sensor data achieved a maximum F1-score of 0.85, with corresponding precision and recall of 0.87 and 0.83 respectively.
    PHMs also achieved a maximum F1-score of 0.85, with corresponding precision and recall of 0.87 and 0.83 respectively.

Prognosis
    Raw sensor data achieved a maximum F1-score of 0.80, with corresponding precision and recall of 0.85 and 0.77 respectively.
    PHMs achieved a maximum F1-score of 0.83, with corresponding precision and recall of 0.83 and 0.83 respectively. From these results we can conclude that the PHMs have excellent clinical effectiveness, and this is attributable to the premise that PHMs effectively capture the major abnormal trends for a first level clinical diagnosis and suppress details that can be deferred for a subsequent detailed investigation.

C. Clinical Evaluation: Alerts Engine

Continuing with the same dataset as above, we evaluate the clinical performance of CMI based alerts computed using equation 3. Using PHMs, the CMI based technique generated 42 alerts for 30 P group patients before the onset of AHE. In comparison, using a simple threshold-based approach, these same patient group generated a whopping 438 alerts. This would have caused fatigue to the attending physicians who would have either set more stringent thresholds or completely ignored them, both of which defeat the very purpose of having alerts.

The above clinical trials and verification involving real patients and expert physicians at a well-established hospital confirm the readiness of our AIM remote monitoring system for real world deployment.

Now, we evaluate our AIM remote monitoring system for its performance suitability in global health deployment.

Performance Suitability for Global Health Deployment

Global health by which term we broadly denote equitable access to healthcare, particularly in remote-rural-developing regions is characterized by significant challenges such as: (a) sparse/intermittent/low bandwidth connectivity on accessible data networks, (b) lack of reliable electrical power supply sources, (c) generally low income population and relatively high cost of healthcare diagnostic devices, and (d) unwillingness of physicians to serve in rural regions and overcrowding in the limited hospital facilities wherever available. We broadly categorize (a) and 9b) as issues related to Accessibility. Item (c) is related to Affordability, and (d) is related to Availability. Sometimes, these are referred to as the 3A's of global health by policy makers. We now evaluate the suitability of our AIM remote health monitoring system to adequately address e each of these 3A's.

A. Accessibility

Bandwidth and power are the two major limiting factors related to data infrastructure in remote rural areas. The data to be transmitted from the AIM Smart-edge to the cloud or physicians should be within the capacity of the available networks. If we were to list the available networks in rural regions for transmission of messages, they would generally be:

1) Mobile/cellular network without data/internet connectivity, i.e., only SMS option is available. The maximum size per message is in the range of 140 Bytes (SMS).

2) Mobile/cellular network with minimal data connectivity such as EDGE, which tops out at around 15 KBps.

3) Emerging IoT networks such as that use narrow-band IoT (NB-IoT) technology, which typically supports up to 30 KBps. In addition to this, we expect further constraints on the bandwidth as the number of IoT nodes scale. We now evaluate the data rates for our risk-stratified message push/pull protocol and the resulting savings in bandwidth and energy.

1) Bandwidth Savings from RASPRO ECG PHMs:

To evaluate the bandwidth requirement for transmission of RASPRO ECG PHMs, we make the following assumptions based on observed clinical practices in our hospital.

The ECG consists of N=5 clinical parameters, namely QRS width, QTc, RR intervals, ST elevation/depression and PR interval.

Severity sampling interval for each parameter is once in a second, and severity is quantized into one of LSV R=8 levels. Each symbol can be represented by Log 2(LSV R)=3 bits.

For each parameter, a consensus symbol is computed for every 60 symbols, and as a result the DSM will have column width of C=60 and number of rows R=N=5 for a total duration of one minute (=60 s). Here, a PHM has to be computed once in every minute. Hence the size of PHMs is given by: Log 2(LSV R)*R=3*5=15 bits/P HM (7) which comes to 900 bits/hour in this case.

In comparison, each minute of the raw sensor data from our AIM-Vitals ECG node generates close to 144 Kb/min, resulting in 80 Mb/hour. Even with use of the most efficient data compression technique, the size of such raw sensor data would be orders of magnitude higher compared to PHMs.

2) Bandwidth Savings from RASPRO BP-SpO2-Pulse Rate PHMs:

To evaluate the bandwidth requirement for transmission of BP, SpO2 and pulse rate PHMs, we make the following assumptions based on observed clinical practices in our hospital.

Severity sampling interval is once per 10s for each parameter and the severity is quantized into one of LSV R=8 levels. Each symbol can be represented by Log 2(LSV R)=3 bits.

For each parameter a consensus symbol is determined for every 60 symbols (spanning 10 minutes) and hence, the DSM will have a column width of C=60 and number of rows R=3 for a total duration of 10 minutes. A PHM has to be computed once in 10 minutes for all N=3 parameters.

Hence the size of PHMs is calculated as:

$$\text{Log } 2(LSV\ R)*R=3*3=9 \text{ bits/P HM} \quad (8)$$

which comes to 54 bits/hour in this case. In comparison, the entire PPG data (100 Hz, 2 channels, bit resolution=22 bits) consumes 4.4 Kb/s, adding up to 15.8 Mb/hour. Also, if all the three parameters were to be transmitted at the common frequency of once in 10 seconds, it would consume 34.6

Kb/hour. Even in this case, the PHMs consumes around 640 times less bandwidth. In this clinical use-case scenario the combined size of ECG, BP, SpO2, and pulse rate PHMs, along with size of headers (such as patient ID, timestamp and location) comes to around 184 bits/min assuming a PHM is computed every minute.

These results demonstrate that PHMs reduce bandwidth usage bringing them within the bandwidth capacities of all the available network options listed in the beginning of this section. The C, R, LSV R values used in these examples are representative numbers and these may be set differently by physicians for varying diagnostic purposes. However, the extent of bandwidth savings would not change noticeably. It might be interesting to observe that even though there is considerable reduction in the bandwidth, there is largely no observable dilution in the diagnostic effectiveness of PHMs as given by the F1-scores in Section VIII on clinical validation.

3) Energy Savings from RASPRO PHMs:

We measure the energy consumption associated with the processing and transmission of RASPRO PHMs. The experimental setup included a low-end Android smartphone (running Android 5.1, 1.2 GHz, 1 GB RAM) as the AIM Smart-edge and Amazon cloud services (S3) for remote storage instantiated with dual core 3.1 GHz processor and 4 GB RAM running Ubuntu 14.04. The energy measurements were taken for different durations of ECG data and reported in FIG. 16.

Figure 16:
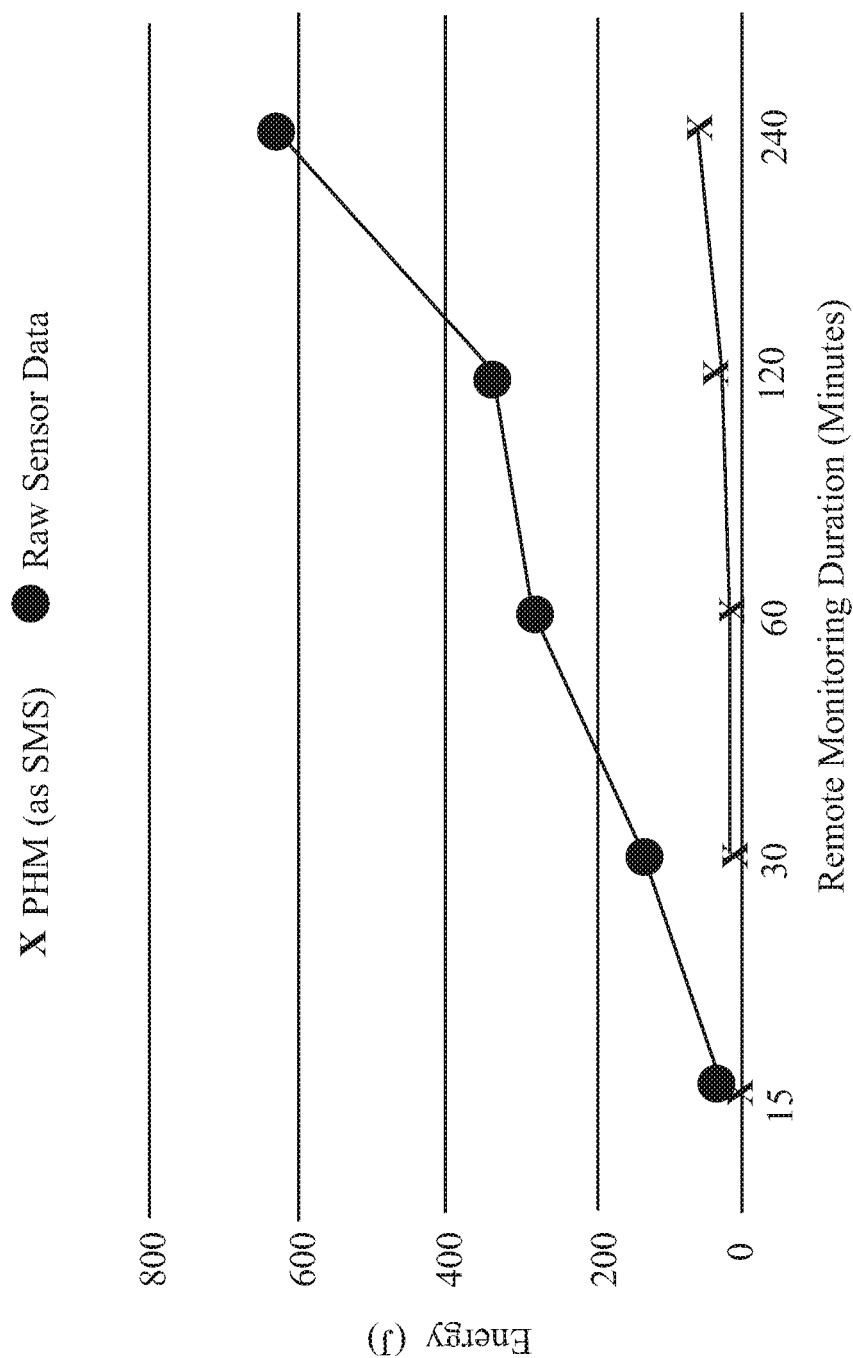
FIG. 16 shows energy measurements taken for different durations of ECG data in an embodiment of the invention.

We observe from the results presented in FIG. 16 that there is big energy savings (averaging 90%) in using RASPRO PHMs in comparison to raw sensor data. Such energy savings are becoming indispensable for ubiquitous deployment of IoT based sensors and devices.

B. Affordability

A comparison of AIM-Vitals with commercially available continuous (and non-continuous) cardiac monitoring devices such as Holter Monitor and External Loop Recorder (ELR) shows that AIM-Vitals is at least three times lower in cost; not to mention its superior features. For instance, Holter and ELR do not provide for immediate transmission in case of emergencies, which is a drawback when it comes to remote monitoring of high risk patients. Compared to these three systems, AIM-Vitals provides not just the ECG, BP, SpO2 and Pulse rate measurements, but also real-time activity tagging based on the accelerometer readings from the AIM-Vitals. It also ensures timely transmission of the ECG parameters (in increasing granularity from PHMs to DD-on-D) over low bandwidth cellular/NB-IoT networks, whenever the alerts are in high or critical levels.

RASPRO PHMs also bring in added affordability by means of reduction in recurring data bandwidth usage cost to the patient. Additionally, based on the alert levels, the low and normal patients can forgo unnecessary hospital visits and expensive medical procedures. This will, in effect, result in overall reduction of healthcare service delivery cost in global health setting.

C. Availability

The risk-stratified alerts mechanism that we presented in Section VII segregates the patients into four levels among which the physician can focus his consultative time and in-person attention only towards critical/high alert patients. Whereas, for those who do not require the physician's attention as assessed by low & normal alert levels, need not go in for unnecessary hospital re-visits.

We attempt to quantify the potential increase in availability using our AIM Smart-edge remote monitoring system, and we define the following:

P=total number of patients that are accommodated by the physician per month
P new=number of new patients among P
Prev=number of revisit patients among P We note that the revisit patients are given priority over new patients and hence many new patients are unable to get an appointment.

In the absence of AIM remote monitoring: The total number of patients accommodated by the physician in a month is given by:

$$P = Pnew + Prev \quad (9)$$

In presence of AIM remote monitoring: The total number of patients accommodated by the physician in a month would be:

$$P = P\text{ rem new} + Prev\text{ rem} \quad (10)$$

In the presence of AIM remote monitoring, since, only those who are having high/critical alert levels need to revisit the hospital, the total number of revisit patients (termed as Prev rem) becomes lesser than P rev. Hence, Prev–Prev rem is the increase in availability of the physician for new patients. In our hospital setting in the cardiology department, the observed average numbers for the above variables, in the absence of AIM remote monitoring, are: P=720, Pnew=288, Prev=432. In our surveys, we observed that 60% of the P rev patients who travel more than 200 km from their villages, come with no change in their clinical diagnosis/situation. They could have avoided such unnecessary hospital review revisits.

Hence, in the presence of remote monitoring, the total number of new patients that the physician could accommodate to see in a month would be:

$$P\text{ rem new} = P - Prev\text{ rem} = 720 - (0.60*(Prev)) = 720 - (0.60*432) = 460.$$

Comparing Pnew against Pnew rem, we see that by employing our AIM Smart-edge remote monitoring, we could potentially increase the availability of physicians by up to 59% to see new patients as well as returning high risk patients by freeing their consultative time otherwise spent on low-risk/normal patients. This is corroborated by Martnez-Ramos et al who report similar improvements in reduction of revisit patients with the use of a remote monitoring system.

CONCLUSION

Global health, with its triple challenges of accessibility, affordability, and availability, is a vast arena for technological intervention by IoT based remote health monitoring. In this paper, we have taken a significant step towards developing a novel IoT based smart edge architecture for remote health monitoring, in which we have migrated the medical domain-based smarts into the IoT smart edge. This is accomplished through two high performance software engines, namely RASPRO and CMI, both running on the IoT smart edge. RASPRO transforms voluminous sensor data into clinically relevant summaries in the form of Personalized Health Motifs (PHMs) and alerts. The PHMs and alerts are then sent to the physicians based on a risk-stratified push/pull protocol using the best combination of cellular/mobile/NB-IoT networks. The clinical validation through deployment in our hospital, and remote telemedicine location has demonstrated that AIM Vitals could be a potential low-cost, yet feature rich, alternative to existing clinical grade devices for remote monitoring. We have also clinically shown that PHMs are as good as raw sensor data in prognosis and diagnosis of AHE and AF disease conditions as given by precision, recall, and F1-score scores of 0.87, 0.83, and 0.85 respectively. Our system performance evaluation has shown remarkable improvements in bandwidth (98%) and energy (90%) utilization in the AIM Smart-edge using PHMs. AIM Smart-edge can significantly reduce the data load both in the network as well as at the physician's end.

Furthermore, the initial pilot study in our University hospital showed that the AIM Smart-edge could potentially improve the availability of physicians for patients by up to 59%. Hence, the AIM Smart-edge based remote health monitoring is well suited for bridging the global health equity gap.

Although the detailed description contains many specifics, these should not be construed as limiting the scope of the invention but merely as illustrating different examples and aspects of the invention. While the invention has been disclosed with reference to certain embodiments, it will be understood by those skilled in the art that various changes may be made, and equivalents may be substituted without departing from the scope of the invention. In addition, many modifications may be made to adapt to a particular situation or material to the teachings of the invention without departing from its scope.

What is claimed is:

1. A health-monitoring system, comprising:
   IoT-vitals sensing nodes joined to a patient's body, sensing vital characteristics, employing wireless transmission circuitry transmitting sensed data by a short-range network; and
   a local gateway having wireless circuitry receiving transmitted data from the IoT-vitals sensors, software (SW) executing on a processor from a non-transitory medium, the SW comprising a first program accomplishing rapid summarization of data as personalized health motifs (PHM), and a second program computing criticality alerts from the PHM data, and transmission circuitry transmitting the PHM data on a long-range network to a cloud-storage and processing center, and the criticality alerts by a second network to doctor's platforms.

2. The system of claim 1 wherein the sensing nodes comprise at least one electrocardiology (ECG) sensor and at least one photoplethysmography (PPG) sensor.

3. The system of claim 1 wherein one sensor is configured as a master sensor and one or more other sensors are configured as slave sensors, the master sensor receiving data from the slave sensors and transmitting the received data to the gateway.

4. The system of claim 1 wherein the short-range network is one of ZigBee™, Bluetooth™ or WiFi.

5. The system of claim 1 wherein the long-range network is one of a cellular network, a radio-frequency network or the Internet network.

6. The system of claim 1 wherein the gateway is accomplished by a smartphone executing software providing functions of the gateway.

7. The system of claim 1 wherein the doctor's platforms execute Android-based SW enabling the doctors to receive and visualize patient data, and to suggest interventions remotely to the patients or their caretakers.

8. The system of claim 7 wherein the Android-based SW also enable the doctors to set and tune sensing frequency, transmission timing, summarization intervals, and other variables in the system.

9. The system of claim 1 wherein the cloud broadly hosts a Hospital Information System (HIS) software suite and data storage which is a publicly available CCHIT certified J2EE based health informatics suite.

10. The system of claim 9 wherein HIS serves as an archival database storage for all patient records with access control, security, privacy, and reliability.

11. The system of claim 10 wherein HIS additionally supports running special purpose data analytics algorithms on anonymized patient data.

12. A method for monitoring a patient's vital medical characteristics, comprising:
    joining IoT-vitals sensing nodes to the patient's body, sensing vital characteristics;
    transmitting sensed data to a gateway by a short-range network;
    receiving the transmitted data at the gateway;
    accomplishing rapid summarization of data as personalized health motifs (PHM) by a first program executing on the gateway;
    computing criticality alerts from the PHM data by a second program executing on the gateway; and
    transmitting the summarized data to a cloud-storage and processing center over a long-range network, and the criticality alerts to doctor's platforms by a second network.

13. The method of claim 12 comprising sensing electrocardiology (ECG) data by one sensing node, and sensing photoplethysmography (PPG) data by another sensor.

14. The method of claim 12 comprising one sensor operating as a master sensor, and one or more other sensors operating as slave sensors, the master sensor receiving data from the slave sensors and transmitting the received data to the gateway.

15. The method of claim 12 wherein sensors transmit by one of ZigBee™, Bluetooth™ or WiFi protocol.

16. The method of claim 12 wherein the gateway transmits by one of cellular, radio frequency or Internet protocol.

17. The method of claim 12 wherein the gateway is accomplished by a smartphone executing software providing functions of the gateway.

18. The method of claim 12 wherein the doctor's platforms execute Android-based SW enabling the doctors to receive and visualize patient data, and to suggest interventions remotely to the patients or their caretakers.

19. The method of claim 18 wherein the Android-based SW also enables the doctors to set and tune sensing frequency, transmission timing, summarization intervals, and other variables in the system.

20. The method of claim 12 wherein the cloud broadly hosts a Hospital Information System (HIS) software suite and data storage which is a publicly available CCHIT certified J2EE based health informatics suite.

21. The method of claim 20 wherein HIS serves as an archival database storage for all patient records with access control, security, privacy, and reliability.

22. The method of claim 21 wherein HIS additionally supports running special purpose data analytics algorithms on anonymized patient data.

* * * * *